US007195710B2

(12) United States Patent
Bomberger et al.

(10) Patent No.: US 7,195,710 B2
(45) Date of Patent: *Mar. 27, 2007

(54) SYSTEMS AND METHODS USING MULTIPLE SOLVENTS FOR THE REMOVAL OF LIPIDS FROM FLUIDS

(75) Inventors: David C. Bomberger, Belmont, CA (US); Bryan Chavez, San Jose, CA (US); Pablo E. Garcia, Redwood City, CA (US); Eric Hegwer, Menlo Park, CA (US); Thomas P. Low, Belmont, CA (US); Ripudaman Malhotra, San Carlos, CA (US); Jeffrey J. Shimon, Mountain View, CA (US)

(73) Assignee: Lipid Sciences, Inc., Pleasanton, CA (US)

( * ) Notice: Subject to any disclaimer, the term of this patent is extended or adjusted under 35 U.S.C. 154(b) by 329 days.

This patent is subject to a terminal disclaimer.

(21) Appl. No.: 10/856,046

(22) Filed: May 28, 2004

(65) Prior Publication Data

US 2004/0217047 A1 Nov. 4, 2004

Related U.S. Application Data

(62) Division of application No. 10/178,900, filed on Jun. 21, 2002, now Pat. No. 7,033,500.

(60) Provisional application No. 60/301,112, filed on Jun. 25, 2001, provisional application No. 60/301,108, filed on Jun. 25, 2001, provisional application No. 60/300,927, filed on Jun. 25, 2001, provisional application No. 60/301,109, filed on Jun. 25, 2001, provisional application No. 60/346,094, filed on Jan. 2, 2002.

(51) Int. Cl.
*B01D 63/02* (2006.01)
*B01D 36/00* (2006.01)
*B01D 11/04* (2006.01)
*B01D 11/00* (2006.01)

(52) U.S. Cl. .......... 210/257.2; 210/252; 210/253; 210/255; 210/263; 210/321.79; 210/321.8; 210/645; 210/650; 210/660; 210/804; 210/805; 210/806; 210/807; 604/5.03

(58) Field of Classification Search ............... 210/252, 210/253, 255, 257.2, 263, 321.79, 321.8, 210/645, 649, 650, 660, 804, 805, 806, 807; 604/5.03
See application file for complete search history.

(56) References Cited

U.S. PATENT DOCUMENTS 3,647,624 A 3/1972 Evenson (Continued)

FOREIGN PATENT DOCUMENTS

CA 1 271 708 7/1990

(Continued)

OTHER PUBLICATIONS

Aloia, et al., Lipid Composition and Fluidity of the Human Immunodeficiency Virus Envelope and Host Cell Plasma Membranes, Proc. Natl. Acad. Sci. U.S.A., Jun. 1993, pp. 5181-5185, vol. 90.

(Continued)

*Primary Examiner*—Krishnan S. Menon
(74) *Attorney, Agent, or Firm*—Kilpatrick Stockton LLP

(57) ABSTRACT

This invention is directed to systems and methods for removing lipids from a fluid or from lipid-containing organisms from a fluid, such as plasma. These systems combine a fluid with at least one extraction solvent, which causes the lipids to separate from the fluid or from the lipid-containing organisms. The separated lipids are removed from the fluid. The at least one extraction solvent is removed from the fluid or at least reduced to a concentration enabling the fluid to be administered to a patient without undesirable consequences. Once the fluid has been processed, the fluid may be administered to a patient who donated the fluid or to a different patient for therapy.

18 Claims, 18 Drawing Sheets

U.S. PATENT DOCUMENTS

| | | |
|---|---|---|
| 3,958,939 A | 5/1976 | Jones |
| 3,983,008 A | 9/1976 | Shinozaki et al. |
| 3,989,466 A | 11/1976 | Pan |
| 4,025,423 A | 5/1977 | Stonner et al. |
| 4,103,685 A | 8/1978 | Lupien et al. |
| 4,124,509 A | 11/1978 | Iijima et al. |
| 4,234,317 A | 11/1980 | Lucas et al. |
| 4,235,602 A | 11/1980 | Meyer et al. |
| 4,258,010 A | 3/1981 | Rozsa et al. |
| 4,350,156 A | 9/1982 | Malchesky et al. |
| 4,391,711 A | 7/1983 | Jackson et al. |
| 4,397,747 A | 8/1983 | Ikeda |
| 4,399,217 A | 8/1983 | Holmquist et al. |
| 4,402,940 A | 9/1983 | Nose et al. |
| 4,435,289 A | 3/1984 | Breslau |
| 4,463,988 A | 8/1984 | Bouck et al. |
| 4,481,189 A | 11/1984 | Prince |
| 4,522,809 A | 6/1985 | Adamowicz et al. |
| 4,540,401 A | 9/1985 | Marten |
| 4,540,573 A | 9/1985 | Neurath et al. |
| 4,581,231 A | 4/1986 | Purcell et al. |
| 4,591,505 A | 5/1986 | Prince |
| 4,613,501 A | 9/1986 | Horowitz |
| 4,615,886 A | 10/1986 | Purcell et al. |
| 4,643,718 A | 2/1987 | Marten |
| 4,645,512 A | 2/1987 | Johns |
| 4,647,280 A | 3/1987 | Maaskant et al. |
| 4,648,974 A | 3/1987 | Rosskopf et al. |
| 4,658,012 A * | 4/1987 | Altorfer .............. 528/497 |
| 4,668,398 A | 5/1987 | Silvis |
| 4,671,909 A | 6/1987 | Torobin |
| 4,676,905 A | 6/1987 | Nagao et al. |
| 4,677,057 A | 6/1987 | Curtiss et al. |
| 4,680,320 A | 7/1987 | Uku et al. |
| 4,696,670 A | 9/1987 | Ohnishi et al. |
| 4,775,483 A | 10/1988 | Mookerjea et al. |
| 4,832,034 A | 5/1989 | Pizziconi et al. |
| 4,836,928 A | 6/1989 | Aoyagi et al. |
| 4,879,037 A | 11/1989 | Utzinger |
| 4,895,558 A | 1/1990 | Cham |
| 4,908,354 A | 3/1990 | Seidel et al. |
| 4,909,940 A | 3/1990 | Horowitz et al. |
| 4,909,942 A | 3/1990 | Sato et al. |
| 4,923,439 A | 5/1990 | Seidel et al. |
| 4,935,204 A | 6/1990 | Seidel et al. |
| 4,966,709 A | 10/1990 | Nose et al. |
| 4,970,144 A | 11/1990 | Fareed et al. |
| 5,026,479 A | 6/1991 | Bikson et al. |
| 5,080,796 A | 1/1992 | Nose et al. |
| 5,089,602 A | 2/1992 | Isliker et al. |
| 5,112,956 A | 5/1992 | Tang et al. |
| 5,116,307 A | 5/1992 | Collins |
| 5,126,240 A | 6/1992 | Curtiss |
| 5,128,318 A | 7/1992 | Levine et al. |
| 5,152,743 A | 10/1992 | Gorsuch et al. |
| 5,187,010 A | 2/1993 | Parham et al. |
| 5,203,778 A | 4/1993 | Boehringer et al. |
| 5,211,850 A | 5/1993 | Shettigar et al. |
| 5,236,644 A | 8/1993 | Parham et al. |
| 5,256,767 A | 10/1993 | Salk et al. |
| 5,258,149 A | 11/1993 | Parham et al. |
| 5,279,540 A | 1/1994 | Davidson |
| 5,301,694 A | 4/1994 | Raymond et al. |
| 5,354,262 A | 10/1994 | Boehringer et al. |
| 5,391,143 A | 2/1995 | Kensey |
| 5,393,429 A | 2/1995 | Nakayama et al. |
| 5,401,415 A | 3/1995 | Rauh et al. |
| 5,401,466 A | 3/1995 | Foltz et al. |
| 5,418,061 A | 5/1995 | Parham et al. |
| 5,419,759 A | 5/1995 | Naficy |
| 5,424,068 A | 6/1995 | Filip |
| 5,476,715 A | 12/1995 | Otto |
| 5,484,396 A | 1/1996 | Naficy |
| 5,496,637 A | 3/1996 | Parham et al. |
| 5,523,096 A | 6/1996 | Okarma et al. |
| 5,529,933 A | 6/1996 | Young et al. |
| 5,565,203 A | 10/1996 | Gluck et al. |
| 5,634,893 A | 6/1997 | Rishton |
| 5,637,224 A | 6/1997 | Sirkar et al. |
| 5,652,339 A | 7/1997 | Lerch et al. |
| 5,679,260 A | 10/1997 | Boos et al. |
| 5,698,432 A | 12/1997 | Oxford |
| 5,707,673 A | 1/1998 | Prevost et al. |
| 5,719,194 A | 2/1998 | Mann et al. |
| 5,744,038 A | 4/1998 | Cham |
| 5,753,227 A | 5/1998 | Strahilevitz |
| 5,834,015 A | 11/1998 | Oleske et al. |
| 5,853,725 A | 12/1998 | Salk et al. |
| 5,855,782 A | 1/1999 | Falkenhagen et al. |
| 5,858,238 A | 1/1999 | McRea et al. |
| 5,877,005 A | 3/1999 | Castor et al. |
| 5,879,685 A | 3/1999 | Gluck et al. |
| 5,885,578 A | 3/1999 | Salk et al. |
| 5,891,432 A | 4/1999 | Hoo |
| 5,895,650 A | 4/1999 | Salk et al. |
| 5,911,698 A | 6/1999 | Cham |
| 5,916,806 A | 6/1999 | Salk et al. |
| 5,919,369 A | 7/1999 | Ash |
| 5,928,930 A | 7/1999 | Salk et al. |
| 5,948,441 A | 9/1999 | Lenk et al. |
| 5,962,322 A | 10/1999 | Kozarsky et al. |
| 5,980,478 A | 11/1999 | Gorsuch et al. |
| 6,004,925 A | 12/1999 | Dasseux et al. |
| 6,017,543 A | 1/2000 | Salk et al. |
| 6,022,333 A | 2/2000 | Kensey |
| 6,037,323 A | 3/2000 | Dasseux et al. |
| 6,037,458 A | 3/2000 | Hirai et al. |
| 6,039,946 A | 3/2000 | Strahilevitz |
| 6,046,166 A | 4/2000 | Dasseux et al. |
| 6,080,778 A | 6/2000 | Yankner et al. |
| 6,127,370 A | 10/2000 | Smith et al. |
| 6,136,321 A | 10/2000 | Barrett et al. |
| 6,139,746 A | 10/2000 | Kopf |
| 6,156,727 A | 12/2000 | Garber et al. |
| 6,165,502 A | 12/2000 | Oleske et al. |
| 6,171,373 B1 | 1/2001 | Park et al. |
| 6,193,891 B1 | 2/2001 | Kent et al. |
| 6,264,623 B1 | 7/2001 | Strahilevitz |
| 6,309,550 B1 | 10/2001 | Iversen et al. |
| 6,337,368 B1 | 1/2002 | Kobayashi et al. |
| 6,440,387 B1 | 8/2002 | Yankner et al. |
| 6,472,421 B1 | 10/2002 | Wolozin |
| 6,605,588 B1 | 8/2003 | Lees et al. |
| 6,706,008 B2 | 3/2004 | Vishnoi et al. |
| 6,737,066 B1 | 5/2004 | Moss |
| 6,913,696 B1 | 7/2005 | Korngold et al. |
| 2001/0028895 A1 | 10/2001 | Bisgaier et al. |
| 2002/0055529 A1 | 5/2002 | Bisgaier et al. |
| 2002/0081263 A1 | 6/2002 | Yankner et al. |
| 2002/0107173 A1 | 8/2002 | Friedhoff et al. |
| 2002/0183379 A1 | 12/2002 | Yankner et al. |
| 2002/0188012 A1 | 12/2002 | Bisgaier et al. |
| 2003/0018013 A1 | 1/2003 | Dasseux et al. |

FOREIGN PATENT DOCUMENTS

| | | |
|---|---|---|
| CN | 1189378 | 8/1998 |
| DE | 29 44 138 A1 | 6/1981 |
| DE | 31 18 072 A1 | 11/1982 |
| DE | 32 13 390 A1 | 10/1983 |
| DE | 33 10 263 A1 | 9/1984 |
| EP | 0 036 283 A2 | 9/1981 |
| EP | 0 267 471 A1 | 5/1988 |
| FR | 2 571 971 A1 | 4/1986 |

| GB | 183 506 | 3/1970 |
| JP | 127104 | 1/1980 |
| JP | 277303 | 10/1993 |
| SU | 1116396 A | 9/1984 |
| SU | 1204224 A | 1/1986 |
| SU | 1752187 A3 | 7/1992 |
| WO | WO 88/09345 A1 | 12/1988 |
| WO | WO 95/03840 A1 | 2/1995 |
| WO | WO 99/38498 A1 | 8/1999 |
| WO | WO 2000/057995 A1 | 10/2000 |
| WO | WO 01/45718 A1 | 6/2001 |
| WO | WO 01/56579 A1 | 8/2001 |
| WO | WO 02/010768 A3 | 2/2002 |
| WO | WO 02/30863 A2 | 4/2002 |
| WO | WO 02/062824 A2 | 8/2002 |

OTHER PUBLICATIONS

Blanche et al., "Characterization of Complexes of Egg Yolk Phosphatidylcholine and Apolipoprotein A-II Prepared in the Absence and Presence of Sodium Chotate", Biochimica et Biophysica Acta, 1988, pp. 143-152, vol. 958.

Clay et al., "Formation of Apolipoprotien-Specific High-Density Lipoprotien Particels from Lipid-Free Apolipoproteins A-I and AII", Biochem Journal, 1999, pp. 445-451, vol. 337.

Dass et al, Apolipoprotein A-I, Phospholipid Vesicles, and Cyclodextrins as Potential Anti-Atherosclerotic Drugs: Delivery, Pharmacokinetics, and Efficacy, 2000, pp. 161-182, vol. 7.

Durbin, et al., "Lipid-Free Apolipoproteins A-I and A-II Promote Remodeling of Reconstituted High Density Lipoproteins and Alter Theri Reactivity with Lecithin: Cholestoral Acyltransferase", 1999, pp. 2293-2302. vol. 40.

Durbin, et al., "The Effect of Apolipoprotein A-II on the Structure and Function of Apolipoprotein A-I in a Homogeneous Reconstituted High Density Lipoprotein Particle", The Journal of Biological Chemistry, 1997, pp. 31333-31339, vol. 272, No. 50.

Feinstone, Inactivation of Hepatitis B Virus and Non-A, Non-B Hepatitus by Chloroform, 1983, pp. 816-821, vol. 41.

Ito et al, Cholesterol-Sphlongomyelin Interaction in Membrane and Apolipoprotein-Mediated Cellular Cholesterol Eflux, Journal of Lipid Research, 2000, pp. 894-904, vol. 41.

Matz et al., "Reaction of Human Lecithin Cholesterol Acyltransferase with Synthetic Micellar Complexes of Apolipoprotein A-I, Phosphatidylcholine, and Cholesterol", The Journal of Biological Chemistry, 1982, pp. 4541-4546, vol. 257, No. 8.

Nester, et al. Microbiology, 1983, pp. 585.

Neurath et al. Properties of Delipidated Hepatitis B Surface Antigen (HBsAg) and Preparation of Its Proteolytic Cleavage Fragments Carrying HbsAg-Specific Antigenic Determinants, Invervirology, 1978, pp. 265-275, vol. 10.

Osborne, et al., "Delipidation of Plasma Lipoproteins", Methods in Enzymology, 1986, pp. 213-222, vol. 128.

Rye, et al. "Changes in the Size of Reconstituted High Density Lipoproteins During Incubation with cholesteryl Ester Transfer Protein: the role of Apolipoproteins", 1992, pp. 215-224. vol. 33.

Walker, et al., "Escape from the Immune System", Nature, Sep. 21, 2000, pp. 313-314, vol. 407.

Agnese, et al., Clinical Biochemistry, Evaluation of four Reagents for Delipidation of Serum, 16, 98-100. (1983).

Albouz, et al., Ann. Biol. Clin., Extraction of Plasma Lipids Preserving Antigenic Properties of Proteins and Allowing Quantitation of Gangliosides by Neuraminic Acid Determination, 37, 287-290. (abstract only) (1979).

Andre et al., Journal of Virology, Characterization of Low- and Very-Low-Density Hepatitis C Virus RNA-Containing Particles, 76 (14), 6919-6928. (Jul. 2002).

Asziaios et al., Arterioscier. Thromb. Vasc. Biol., Distribution of Apo A-I-Containing HDL Subpopulations in Patients with Coronary Heart Disease, 2670-2676. (Dec. 1, 2000).

Asziaios et al., Arterioscier. Thromb. Vasc. Biol., Presence and Formation of 'Free Apolipoprotein A-1-Like' Particles in Human Plasma, 15, 1419-1423. (1995).

Asziaios et al., Arterioscier. Thromb. Vasc. Biol., Role of Free Apolipoprotein A-I in Cholesterol Efflux, 17, 1630-1636. (1997).

Badimon, et al., Laboratory Investigation, High Density Lipoprotein Plasma Fractions Inhibit Aortic Fatty Streaks In Cholesterol-Fed Rabbits, 60, 455-461. (1989).

Badimon, et al., J. Clinical Investigation, Regression of Atherosclerotic Lesions by High Density Lipoprotein Plasma Fraction in the Cholesterol-Fed Rabbit, 85, 1234-1241. (1990).

Barrans et al., Biochimica et Biophysica Acta, Pre-β HDL: Structure and Metabolism, 1300, 73-85. (1996).

Barres et al., Science, Cholesterol—Making or Breaking the Synapse, 294, 1296-1297. (Nov. 9, 2001).

Bloom, et al., Clin. Biochem., Quantitation of lipid profiles from isolated serum lipoproteins using small volumes of human serum, 14, 119-125. (abstract only) (Jun. 1981).

Burns et al., Neurochem Res, Use of In Vivo Models to Study the Role of Cholesterol in teh Etiology of Alzheimer's Disease 28, 979-86. (abstract only) (Jul. 2003).

Cham, Clinical Chemistry, Nature of the Interaction Between Low-Density Lipoproteins and Polyanions and Metal Ions, as Exemplified by Heparin and $Ca^{2+}$, 22, 1812-1816. (1976).

Cham, et al., J. of Lipid Research, A Solvent System for Delipidation of Plasma or Serum Without Protein Precipitation, 17, 176-181. (1976).

Cham, et al., Clinical Chemistry, Changes in Electrophoretic Mobilities of α- and β-Lipoproteins as a Result of Plasma Delipidation, 22, 305-309. (1976).

Cham, et al., Biochemical and Biophysical Research Communications, Heterogeneity of Lipoprotein B, 103, 196-206. (1981).

Cham, et al., Chem. Biol. Interactions, Importance of Apolipoproteins in Lipid Metabolism, 20, 263-277. (1978).

Cham, et al., J. Biol. Chem., In Vitro Partial Relipidation of Apolipoproteins in Plasma, 251, 6367-6371. (abstract only) (1976).

Cham, et al., Pharmacol. (Life Sci. Adv.), Lipid Apheresis in an Animal Model Causes Acute Reduction in plasma Lipid Concentrations and Mobilisation of Lipid from Liver and Aorta, 13, 25-32. (1994).

Cham, et al., J. Clin. Apheresis, Lipid Apheresis in an Animal Model causes In Vivo Changes in Lipoprotein Electrophoretic Patterns, 11, 61-70. (1996).

Cham, et al., J. Clin. Apheresis, Lipid Apheresis: An In Vivo Application of Plasma Delipidation with Organic Solvents Resulting in Acute Transient Reduction of Circulating Plasma Lipids in Animals, 10, 61-69. (1995).

Cham, et al., Clinical Chemistry, Phospholipids in EDTA—Treated Plasma and Serum, 39, 2347-2348. (1993).

Cham, et al., 59th Congress European Atherosciersosis Society, Nice, France, Rapid Regression of Atherosciersois by Cholesterol Apheresis—A Newly Developed Technique, 17-21. (abstract only) (May 1992).

Cham, et al., Clinica Chimica Acta, Rapid, Sensitive Method for the Separation of Free Cholesterol from Ester Cholesterol, 49, 109-113. (1973).

Collet et al., Journal of Biological Chemistry, Differential Effects of Lecithin and Cholesterol on the Immunoreactivity and Confirmation of Apolipoprotein A-I in High Density Lipoproteins, 266 (14), 9145-9152. (May 15, 1991).

Cooper, Drugs Aging, Dietary Lipids in the Aetiology of Alzheimer's disease: Implications for Therapy, 20 (6), 399-418. (abstract only) (2003).

Cruzado et al., Analytical Biochemistry, Characterization and Quantitiation of the Apoproteins of High-Density Lipoprotein by Capillary Electrophoresis, 14 (7), 100-109. (1996).

Deva, et al., J. Hosp. Infect., Establishment of an in-use testing method for evaluating disinfection of surgical instruments using the duck hepatitis B model, 22, 119-130. (abstract only) (Jun. 1996).

Dwivedy, 18th Australian Atherosciersosis Society Conference, Surfers Paradise, Increase of Reverse Cholesterol Transport by Cholesterol Apheresis Regression of Atherosciersosis, 21. (1992).

Eisenhauer, et al, Klin Wochenschr (KWH), Selective Removal of Low Density Lipoproteins (LDL) by Precipitation at Low pH: First Clinical Application of the HELP System 65, 161-168. (1987).

Fang, et al., 18th Australian Atheroscierosis Society Conference, Gold Coast, Australia, In Vivo Rapid Mobilization of Adipose Tissue by Lipid Apheresis—A Newly Developed Technique. (1992).

Feinstone, et al., Infection and Immunity, Inactivation of Hepatitis B Virus and Non-A, Non-B Hepatitis by Chloroform, 41, 816-821. (Aug. 1983).

Golde et al., Drug Discovery Today, Cholesterol Modulation as an Emerging Strategy for the Treatment of Alzheimer's Disease, 6 (20), 1049-1055. (abstract only) (Oct. 15, 2001).

Hatch et al., Lipoprotein Analysis, Advances in Lipid Research, Practical Methods for Plasma Lipoprotein Analysis, 6, 1-68. (1968).

Horowitz, et al., Blood Coagulation and Fibrinolysis, Viral safety of solvent/detergent-treated blood products, 5, S21-S28. (1994).

Innerarity, et al., Biochemistry, Enhanced Binding by Cultured Human Fibroblasts of Apo-E-Containing Lipoproteins as Compared with Low Density Lipoproteins, 17, 1440-1447. (1978).

Jackson et al., Biochimica et Biophysica Acta, Isolation and Characterization of the Major Apolipoprotein from Chicken High Density Lipoproteins, 420, 342-349. (1976).

Klimov, et al., Kardologila, Extraction of Lipids from Blood Plasma and Subsequent Introduction of Autologous Delipidized Plasma into the Body as a Possible Means to Treat Atheroscierosis [translation]. 19, 23-29. (1978).

Koizumi, et al., J. Lipid Research, Behavior of Human Apolipoprotein A-1: Phospho-Lipid and apoHDL: PHospholipid Complexes In Vitro and aFter Injection into Rabbits, 29, 1405-1415. (1988).

Kostner, et al., XI Internet Symp. on Drugs Affecting Lipid Metabolism, Italy, Increase of APO A1 Concentration in Hypercholesteraemic Chickens after Treatment with a Newly Developed Extracorpreal Lipid Elimination. (May 13, 1002).

Kostner, et al., European Journal of Clinical Investigation, Lecithin-cholesterol acyltransferase activity in Normocholesterolaemic and Hypercholesterolaemic Roosters: Modulation by Lipid Apheresis, 27, 212-218. (May 7, 1997).

Koudinov et al., Clin Chim Acta, Alzheimer's Amyloid Beta Interaction with Normal Human Plasma High Density Lipoprotein: Association with Apolipoprotein and Lipids, 270 (2), 75-84. (abstract only) Feb. 23, 1999).

Koudinov et al., Cell Biol Int., Alzheimer's Soluble Amyloid Beta Protein is Secreted by HepG2 Cells as an Apolipoprotein, 21 (5), 265-71. (abstract only) (May 1997).

Koudinov et al., Biochem Biophys Res Commun, Biochemical Characterization of Alzheimer's Soluble Amyloid Beta Protein in Human Cerebrospinal Fluid: Association with High Density Lipoproteins, 223 (3), 592-7. (abstract only) (Jun. 25, 1999).

Koudinov et al., Science, Cholesterol's Role in Synapse Formation, 294, 2213. (Nov. 9, 2001).

Koudinova et al., Soc. Neuroscience Abstract Viewer and Itinerary Planner, Amyloid Beta, Neural Lipids, Cholesterol and Alzheimer's Disease—Abstract No. 21.10. (2002).

Lipid Sciences, http://www.lipidsciences.com/technology.html, Lipid Technology, 1-4 (Aug. 25, 2001).

Lupien, et al., Lancet (LOS), A New Approach to the Management of Familial Hypercholesterolaemia: Removal of Plasma-Cholesterol Based on the Principle of Affinity Chromatography, 1, 1261-1265. (1976).

Mauch et al., Science, CNS Synaptogenesis Promtoed by Glia-Derived Cholesterol, Nov. 9, 2001, 294, 1354-1357.

Moya et al., Arterioscierosis and Thrmobosis, A Cell Culture System for Screening Human Serum for Ability to Promote Cellular Cholesterol Efflux, 14 (7), 1056-1065. (Jul. 1994).

Ngu, Medical Hypotheses, Chronic Infections from the Perspective of Evolution: a Hypothesis, 42, 81-88. (1994).

Ngu, Medical Hypotheses, Human Cancers and Viruses: A Hypothesis for Immune Destruction of Tumours Caused by Certain Enveloped Viruses Using Modified Viral Antigens, 39, 17-21. (1992).

Ngu, Medical Hypotheses, The viral envelope in the evolution of HIV: a hypothetical approach to inducing an effective immune response to the virus, 48, 517-521. (1997).

Okazaki et al., Journal of Chromatography, Biomedical Applications, Improved High-Performance Liquid Chromatographic Method for the Determination of Apolopoproteins in Serum High-Density Lipoproteins, 430, 135-142. (1988).

Parker, et al., Proceedings of the National Academy of Sciences, Plasma High Density Lipoprotein is Increased in Man When Low Density Lipoprotein (LDL) is Lowered by LDL-Pheresis, 83, 777-781. (1986).

Paterno et al., Department of Clinical and Experimental Medicine, Reconstituted High-Density Lipoprotein Exhibits Neuroprotection in Two Rat Models of Stroke. (Abstract only) (Dec. 29, 2003).

Refolo et al., Soc. Neuroscience Abstracts, Cholesterol Metabolism: A Potential Target for Alzheimer's Disease Therapy, 27 (2), 1518. (abstract only) (2001).

Robern et al., Experientia, The Application of Sodium Deoxycholate and Sephacryl-200 for the Delipidation and Separation of Hogh Density Lipoproteins, 38, 437-439. (1982).

Ryan, et al., Clinical Chemistry. An Improved Extraction Procedure for the Determination of Triglycerides and Choelsterol in Plasma or Serum, 13, 769-772. (1967).

Scanu et al., Analytical Biochemistry, Solubility in Aqueous Solutions of Ethanol of the Small Molecular Weight Peptides of the Serum Very Low Density and High Density Lipoproteins: Retevance to the Recovery Problem During Delipidation of Serum Lipoproteins, 44, 576-588. (1971).

Segrest et al., Journal of Bilogical Chemistry, A Detailed Molecular Belt Model for Apolipoprotein A-I in Discoldal High Density Lipoprotein, 274 (45), 31755-31758. (Nov. 5, 1999).

Slater, et al., J. of Lipid Research, A Comparison of Delipidated Sera Used in Studies of Sterol Synthesis by Human Mononuclear Leukocytes, 20, 413-416. (1979).

Slater, et al., Atheroscierosis, The Effect of Delipidated High Density Lipoprotein on Human Leukocyte Sterol Synthesis, 35, 41-49. (1980).

Thompson, et al., Lancet (LOS), Plasma Exchange in the Management of Hormozygous Familial Hypercholesterolaemia, 1, 1208-1211. (1975).

Williams, et al., Proc. Natl. Acad. Sci. USA, Low Density Lipoprotein Receptor-Independent Hepatic Uptake of a Synthetic, Cholesterol-Scavenging Lipoprotein: Implications for the Treatment of Receptor-Deficient Atheroscierosis, 85, 242-246. (1988).

Williams et al., Biochim. Biophys. Act., Uptake of Endogenous Cholesterol by a Synthetic Lipoprotein, 875 (2), 183-194. (Feb. 12, 1986).

Wong, et al, Journal of Lipid Research, Retention of gangliosides in serum delipidated by diisopropyl ether-1-butanol extractuibm 24, 666-669. (1983).

Wormser, Henry, PSC3110—Fall Semester 2002, Lipids.

Yokoyama, et al., Arterioscierosis, Selective Removal of Low Density Lipoprotein by Plasmapheresis in Familial Hypercholesteroiemia, 5, 613-622. (1985).

Yoshidome et al., Artif Organs, Serum Amyloid A and P Protein Levels are Lowered by Dextran Sulfate Cellulose Low-Density Lipoprotein Apheresis, 22 (2), 144-148. (1998).

Zetia, http://www.zetia.com/ezetimbe/zetia/hcp/product_highlights/index.jsp, Zetia (ezetimibe), 1-2. (Jul. 18, 2003).

Zetia, http://www.zetia/com/ezetimibe/zetia.hcp/mechanism_of_action/index.jsp. Zetia: Comptiments Statin with a Unique Mechanism, 1-2. (Jul. 18, 2003).

Zhang et al., Journal of Lipid Research, Characterization of phospholipids in a pre-alpha HDL: Selective Phospholipid Efflux with Apolipoprotein A-I, 39, 1601-1607. (1998).

* cited by examiner

SYSTEMS AND METHODS USING MULTIPLE SOLVENTS FOR THE REMOVAL OF LIPIDS FROM FLUIDS

RELATED APPLICATIONS

This application is a divisional of U.S. patent application Ser. No. 10/178,900 entitled "Systems and Methods Using Multiple Solvents for the Removal of Lipids from Fluids" filed Jun. 21, 2002 now U.S. Pat. No. 7,033,500 which is incorporated herein by reference.

This application claims the benefit of the filing dates of U.S. Provisional Application No. 60/301,112, filed Jun. 25, 2001; U.S. Provisional Patent Application No. 60/301,108, filed Jun. 25, 2001; U.S. Provisional Patent Application No. 60/300,927, filed Jun. 25, 2001; U.S. Provisional Patent Application No. 60/301,109, filed Jun. 25, 2001; and U.S. Provisional Patent Application No. 60/346,094, filed Jan. 2, 2002, all of which are incorporated by reference herein.

FIELD OF THE INVENTION

The present invention relates to systems, apparatuses and methods for the removal of lipids from fluids, especially blood plasma, or from lipid-containing organisms, or both, using extraction solvents. After being processed, the fluid may be administered to an animal or human for therapeutic use such as treatment of arteriosclerosis and atherosclerotic vascular diseases, removal of fat within an animal or human, and reduction of infectivity of lipid-containing organisms.

BACKGROUND OF THE INVENTION

Hyperlipidemia and Arteriosclerosis

Cardiovascular, cerebrovascular, and peripheral vascular diseases are responsible for a significant number of deaths annually in many industrialized countries. One of the most common pathological processes underlying these diseases is arteriosclerosis. Arteriosclerosis is characterized by lesions, which begin as localized fatty thickenings in the inner aspects of blood vessels supplying blood to the heart, brain, and other organs and tissues throughout the body. Over time, these atherosclerotic lesions may ulcerate, exposing fatty plaque deposits that may break away and embolize within the circulation. Atherosclerotic lesions obstruct the lumens of the affected blood vessels and often reduce the blood flow within the blood vessels, which may result in ischemia of the tissue supplied by the blood vessel. Embolization of atherosclerotic plaques may produce acute obstruction and ischemia in distal blood vessels. Such ischemia, whether prolonged or acute, may result in a heart attack or stroke from which the patient may or may not recover. Similar ischemia in an artery supplying an extremity may result in gangrene requiring amputation of the extremity.

For some time, the medical community has recognized the relationship between arteriosclerosis and levels of dietary lipid, serum cholesterol, and serum triglycerides within a patient's blood stream. Many epidemiological studies have been conducted revealing that the amount of serum cholesterol within a patient's blood stream is a significant predictor of coronary disease. Similarly, the medical community has recognized the relationship between hyperlipidemia and insulin resistance, which can lead to diabetes mellitus. Further, hyperlipidemia and arteriosclerosis have been identified as being related to other major health problems, such as obesity and hypertension.

Hyperlipidemia may be treated by changing a patient's diet. However, use of a patient's diet as a primary mode of therapy requires a major effort on the part of patients, physicians, nutritionists, dietitians, and other health care professionals and thus undesirably taxes the resources of health professionals. Another negative aspect of this therapy is that its success does not rest exclusively on diet. Rather, success of dietary therapy depends upon a combination of social, psychological, economic, and behavioral factors. Thus, therapy based only on correcting flaws within a patient's diet is not always successful.

In instances when dietary modification has been unsuccessful, drug therapy has been used as an alternative. Such therapy has included use of commercially available hypolipidemic drugs administered alone or in combination with other therapies as a supplement to dietary control. Hypolipidemic drugs have had varying degrees of success in reducing blood lipid; however, none of the hypolipidemic drugs successfully treats all types of hyperlipidemia. While some hypolipidemic drugs have been fairly successful, the medical community has not found any conclusive evidence that hypolipidemic drugs cause regression of atherosclerosis. In addition, all hypolipidemic drugs have undesirable side effects. As a result of the lack of success of dietary control, drug therapy and other therapies, atherosclerosis remains a major cause of death in many parts of the world.

To combat this disturbing fact, a relatively new therapy has been used to reduce the amount of lipid in patients for whom drug and diet therapies were not sufficiently effective. This therapy, referred to as plasmapheresis therapy or plasma exchange therapy, involves replacing a patient's plasma with donor plasma or more usually a plasma protein fraction. While having been fairly successful, this treatment has resulted in complications due to introduction of foreign proteins and transmission of infectious diseases. Further, plasma exchange undesirably removes many plasma proteins, such as very low-density lipoprotein (VLDL), low-density lipoprotein (LDL), and high-density lipoprotein (HDL).

HDL is secreted from both the liver and the intestine as nascent, disk-shaped particles that contain cholesterol and phospholipids. HDL is believed to play a role in reverse cholesterol transport, which is the process by which excess cholesterol is removed from tissues and transported to the liver for reuse or disposal in the bile. Therefore, removal of HDL from plasma is not desirable.

Other apheresis techniques exist that can remove LDL from plasma. These techniques include absorption of LDL in heparin-agarose beads (affinity chromatography), the use of immobilized LDL-antibodies, cascade filtration absorption to immobilize dextran sulphate, and LDL precipitation at low pH in the presence of heparin. Each method removes LDL but not HDL.

LDL apheresis, however, has disadvantages. For instance, significant amounts of plasma proteins in addition to LDL are removed during apheresis. In addition, LDL apheresis must be performed frequently, such as weekly, to obtain a sustained reduction in LDL-cholesterol. Furthermore, LDL removal may be counterproductive because low LDL levels in a patient's blood may result in increased cellular cholesterol synthesis. Thus, removal of LDL from a patient's blood may have negative side effects.

Yet another method of achieving a reduction in plasma cholesterol in homozygous familial hypercholesterolemia, heterozygous familial hypercholesterolemia and patients with acquired hyperlipidemia is an extracorporeal lipid elimination process, referred to as lipid apheresis. In lipid apheresis, blood is withdrawn from a patient, the plasma is separated from the blood, and the plasma is mixed with a solvent mixture. The solvent mixture extracts lipids from the plasma. Thereafter, the delipidated plasma is recombined with the patient's blood cells and returned to the patient.

More specifically, lipid apheresis results in the removal of fats from plasma or serum. However, unlike LDL apheresis, the proteins (apolipoproteins) that transport lipids remain soluble in the treated plasma or serum. Thus, the apolipoproteins of VLDL, LDL and HDL are present in the treated plasma or serum. These apolipoproteins, in particular apolipoproteins A1 from the delipidated HDL in the plasma or serum, are responsible for the mobilization of unwanted lipids or toxins, such as excessive amounts of deposited lipids including cholesterol in arteries, plaques, and excessive amounts of triglycerides, adipose tissue, and fat soluble toxins present in adipose tissue. These excessive amounts of lipids or toxins are transferred to the plasma or serum, and then bound to the newly assembled apolipoproteins. Application of another lipid apheresis procedure successively removes these unwanted lipids or toxins from the plasma and thus the body. The main advantage of this procedure is that LDL and HDL are not removed from the plasma. Instead, only cholesterol, some phospholipid and a considerable amount of triglycerides are removed.

While lipid apheresis has the potential to overcome the shortcomings of dietary control, drug therapy and other apheresis techniques, existing apparatuses and methods for lipid apheresis do not provide a sufficiently rapid and safe process. Thus, a need exists for systems, apparatuses and methods capable of conducting lipid apheresis more quickly than accomplished with conventional equipment and methods.

Unfortunately, existing lipid apheresis systems suffer from a number of disadvantages that limit their ability to be used in clinical applications, such as in doctors' offices and other medical facilities. One disadvantage is the explosive nature of the solvents used to delipidate this plasma. If used in a continuous system, these solvents are in close proximity to patients and medical staff. Thus, it would be advantageous to limit this exposure; however, this hazard is clearly present for the duration of the delipidation process, which usually runs for several hours.

Another disadvantage is the difficulty in removing a sufficient amount of solvents from the delipidated plasma in order for the delipidated plasma to be safely returned to a patient. In addition, patients are subjected to an increased chance of prolonged exposure to solvents in a continuous system. Furthermore, current techniques do not provide for sequential multi-washes because the volume of blood necessary for continuous processing using conventional equipment requires removal of an amount of blood that would harm the patient. In other words, conventional equipment does not allow for automated continuous removal, processing and return of plasma to a patient in a manner that does not negatively impact total blood volume of the patient. While the long-term toxicity of various extraction solvents is not known, especially when present in the bloodstream, clinicians know that some solvents may cross the blood-brain barrier. Furthermore, external contact with solvents is known to cause clinical symptoms, such as irritation of mucous membranes, contact dermatitis, headaches, dizziness and drowsiness. Therefore, conventional equipment for lipid apheresis is not adequate to conduct continuous processing of a patient's blood.

Infectious Disease

While the medical community has struggled to develop cures for hyperlipidemia and arteriosclerosis, it has likewise struggled in its battle against infectious diseases. Infectious diseases are a major cause of suffering and death throughout the world. Infectious disease of varied etiology affects billions of animals and humans each year and inflicts an enormous economic burden on society. Many infectious organisms contain lipid as a major component of the membrane that surrounds them. Three major classes of organisms that produce infectious disease and contain lipid in their cell wall or envelope include bacteria, viruses, and protozoa. Numerous bacteria and viruses that affect animals and humans cause extreme suffering, morbidity and mortality. Many bacteria and viruses travel throughout the body in fluids, such as blood, and some reside in plasma. These and other infectious agents may be found in other fluids, such as peritoneal fluid, lymphatic fluid, pleural fluid, pericardial fluid, cerebrospinal fluid, and in various fluids of the reproductive system. Disease can be caused at any site bathed by these fluids. Other bacteria and viruses reside primarily in different organ systems or in specific tissues, where they proliferate and enter the circulatory system to gain access to other tissues and organs.

Infectious agents, such as viruses, affect billions of people annually. Recent epidemics include the disease commonly known as acquired immune deficiency syndrome (AIDS), which is believed to be caused by the human immunodeficiency virus (HIV). This virus is rapidly spreading throughout the world and is prevalent in various sub-populations, including individuals who receive blood transfusions, individuals who use needles contaminated with the disease, and individuals who contact infected fluids. This disease is also widespread in certain countries. Currently, no known cure exists.

It has long been recognized that a simple, reliable and economically efficient method for reducing the infectivity of the HIV virus is needed to decrease transmission of the disease. Additionally, a method of treating fluids of infected individuals is needed to decrease transmission of the virus to others in contact with these fluids. Furthermore, a method of treating blood given to blood banks is needed to decrease transmission of the virus through individuals receiving transfusions. Moreover, an apparatus and method are needed for decreasing the viral load of an individual or an animal by treating the plasma of that individual and returning the treated plasma to the individual such that the viral load in the plasma is decreased.

Other major viral infections that affect animals and humans include, but are not limited to meningitis, cytomegalovirus, and hepatitis in its various forms. While some forms of hepatitis may be treated with drugs, other forms have not been successfully treated in the past.

At the present time, most anti-viral therapies focus on preventing or inhibiting viral replication by manipulating the initial attachment of the virus to the T4 lymphocyte or macrophage, the transcription of viral RNA to viral DNA and the assemblage of new virus during reproduction. Such a focus has created major difficulty with existing treatments, especially with regard to HIV. Specifically, the high mutation rate of the HIV virus often renders treatments ineffective shortly after application. In addition, many different strains of HIV have already become or are becoming resistant to anti-viral drug therapy. Furthermore, during anti-viral therapy treatment, resistant strains of the virus may evolve. Finally, many common therapies for HIV infection involve several undesirable side effects and require patients to ingest numerous pills daily. Unfortunately, many individuals are afflicted with multiple infections caused by more than one infectious agent, such as HIV, hepatitis and tuberculosis. Such individuals require even more aggressive and expensive drugs to counteract disease progression. Such drugs may cause numerous 'side effects as well as multi-drug resistance. Therefore, an effective method and apparatus is needed that does not rely on drugs for combating infectious organisms found in fluids.

Thus, a need exists to overcome the deficiencies of conventional systems and methods for removing lipids from fluids such as plasma or serum and for removing lipids from infectious organisms contained in a fluid. Furthermore, a need exists for a medical apparatus and method to perform delipidation rapidly, either in a continuous or discontinuous manner of operation. A need further exists for such an apparatus and process to perform safely and reliably, and to produce delipidated fluid having residual plasma solvent levels meeting acceptable standards. In addition, a need exists for an apparatus having minimal physical connection between a patient and the lipid apheresis process. Furthermore, a need exists for an economical medical apparatus that is sterile and made of a disposable construction for a single use application. Finally, a need exists for such an apparatus and process to be automated, thereby requiring minimal operator intervention during the course of normal operation.

SUMMARY OF THE INVENTION

This invention is directed to systems, apparatuses and methods for removing lipids from fluids containing lipids or from lipid-containing organisms, or both, and more particularly, this invention is directed to the removal of lipids from fluids containing lipids or lipid-containing organisms using multiple solvents. Specifically, these systems are adapted to remove lipids from a fluid or from lipid-containing organisms, or both, by contacting the fluid with at least two solvents in one or more passes through a system.

In general, the systems of this invention receive a fluid that contain lipids or that may contain lipid-containing organisms, or both, from a fluid source, which may be a patient, a container or other source, and contact the fluid with a first extraction solvent provided by a first extraction solvent source. The systems also include at least one device for contacting the fluid with a first extraction solvent and forming a first mixture comprising the fluid and the first extraction solvent, wherein at least a portion of the lipids dissolve in the first extraction solvent. The systems may include at least one first solvent removal device for contacting the first mixture with a second extraction solvent, removing a portion of the first mixture, and forming a second mixture comprising the first extraction solvent, the second extraction solvent and the fluid and at least a portion of the first extraction solvent dissolved in the second extraction solvent. The systems include at least one second solvent removal subsystem for removing at least a portion of the second extraction solvent from the second mixture. The systems may also be configured so that the same device or combination of devices is used for removing lipids from a fluid using a first extraction solvent and for removing the first extraction solvent from the fluid using a second extraction solvent.

The systems perform a method that reduces the concentration of lipids in a fluid or removes lipids from lipid-containing organisms. The systems are composed of three phases, referred to as an initial phase, an intermediate phase, and a final phase. The initial phase includes contacting a first extraction solvent with a fluid. The first extraction solvents permeate the hollow fibers and mix with the fluids within the lumens of the hollow fibers. The first extraction solvent, which may be composed of many different chemicals as defined below, causes at least a portion of the lipids in the fluid or in the lipid-containing organisms to separate from the fluid containing lipids or from the lipid-containing organisms. The first extraction solvent produces a suspension of lipid particles in the first mixture that is formed from the fluid and the first extraction solvent. The solvent disrupts the lipid-protein structure and frees the lipid particles, which are not very soluble in the fluid. A product that results from the initial phase is a first mixture composed of the fluid having at least some lipids separated from the fluid and the first extraction solvent, and a first extraction solvent with dissolved lipids.

The intermediate phase includes contacting the first mixture with a second extraction solvent to remove at least a portion of the first extraction solvent from the first mixture and may separate a portion of lipids remaining in the partially delipidated fluid or in the partially delipidated organisms. The intermediate phase produces a second mixture composed of a partially delipidated fluid and the first and second extraction solvents, and a second extraction solvent including dissolved lipids and a portion of the first extraction solvent. The final phase includes removing at least a portion of the first and second extraction solvents from the second mixture formed during the intermediate phase so that the concentration of the solvents in the delipidated fluid will not cause undesirable consequences in a patient receiving the delipidated fluid.

The systems of this invention perform the initial, intermediate and final phases to produce a fluid or lipid-containing organism having a reduced concentration of lipids. These phases may be performed using systems having many different configurations. For instance, at least one embodiment of this invention uses a different subsystem to perform each of the initial, intermediate, and final phases of the delipidation method. Other embodiments of the invention use a single subsystem to perform both the initial and intermediate phases of the delipidation method and a different subsystem to perform the final phase of the delipidation method. In yet another embodiment, a single device is used to perform all three phases of the delipidation method.

In certain embodiments, a first phase subsystem performs the first phase of the delipidation method. The first phase subsystem may be composed of numerous components, including, but not limited to, at least one hollow fiber contactor (HFC), at least one drip through column (DTC), at least one in-line static mixer, at least one depth filter, a vortexer, a centrifuge, end-over-end rotation of a sealed container, or other suitable devices, or any combination of these devices. The intermediate phase may be performed using either the first phase system with a second extraction solvent or an entirely different subsystem. For instance, the intermediate phase subsystem may be composed of at least one HFC, at least one DTC, at least one in-line static-mixer, a depth filter, a vortexer, a centrifuge, end-over-end rotation of a sealed container, or other suitable device, or any combination of these devices.

The final phase of the delipidation method may be conducted using a final phase subsystem. One embodiment of the final phase system includes at least one HFC for removing the first and second extraction solvents from the fluid. This may be accomplished by passing the second mixture of partially delipidated fluid and first and second extraction solvents through lumens of hollow fibers of the at least one HFC while a gas, such as common air, nitrogen or other gases; a mineral oil; or other materials, is passed through the HFC on the shell side of the hollow fibers, or vice versa. The final phase subsystem may consist of two or more HFCs coupled together in a series or parallel configuration. The first and second extraction solvents in the fluid may be reduced to a desired level by passing the second mixture through the final phase subsystem one or more times depending on the configuration of the system.

An advantage of this invention is that fluids containing lipids or lipid-containing organisms can be processed in a continuous manner and returned to a patient without requiring withdrawal of an unacceptable level of blood from the patient. Furthermore, this invention may be used as a discontinuous or batch system for processing a fluid, such as plasma from a blood bank.

Another advantage of this invention is that the concentration of lipids or lipid-containing organisms, or both, may be reduced in a fluid in a time efficient manner.

Yet another advantage of this invention is that portions of these systems that contact a fluid containing lipids or lipid-containing organisms, or both, during operation are capable of being produced as disposable members, which reduces the amount of time needed between patients to prepare a system for use by another patient.

These and other features and advantages of the present invention will become apparent after review of the following drawings and detailed description of the disclosed embodiments.

DETAILED DESCRIPTION OF THE INVENTION

Figure 1:
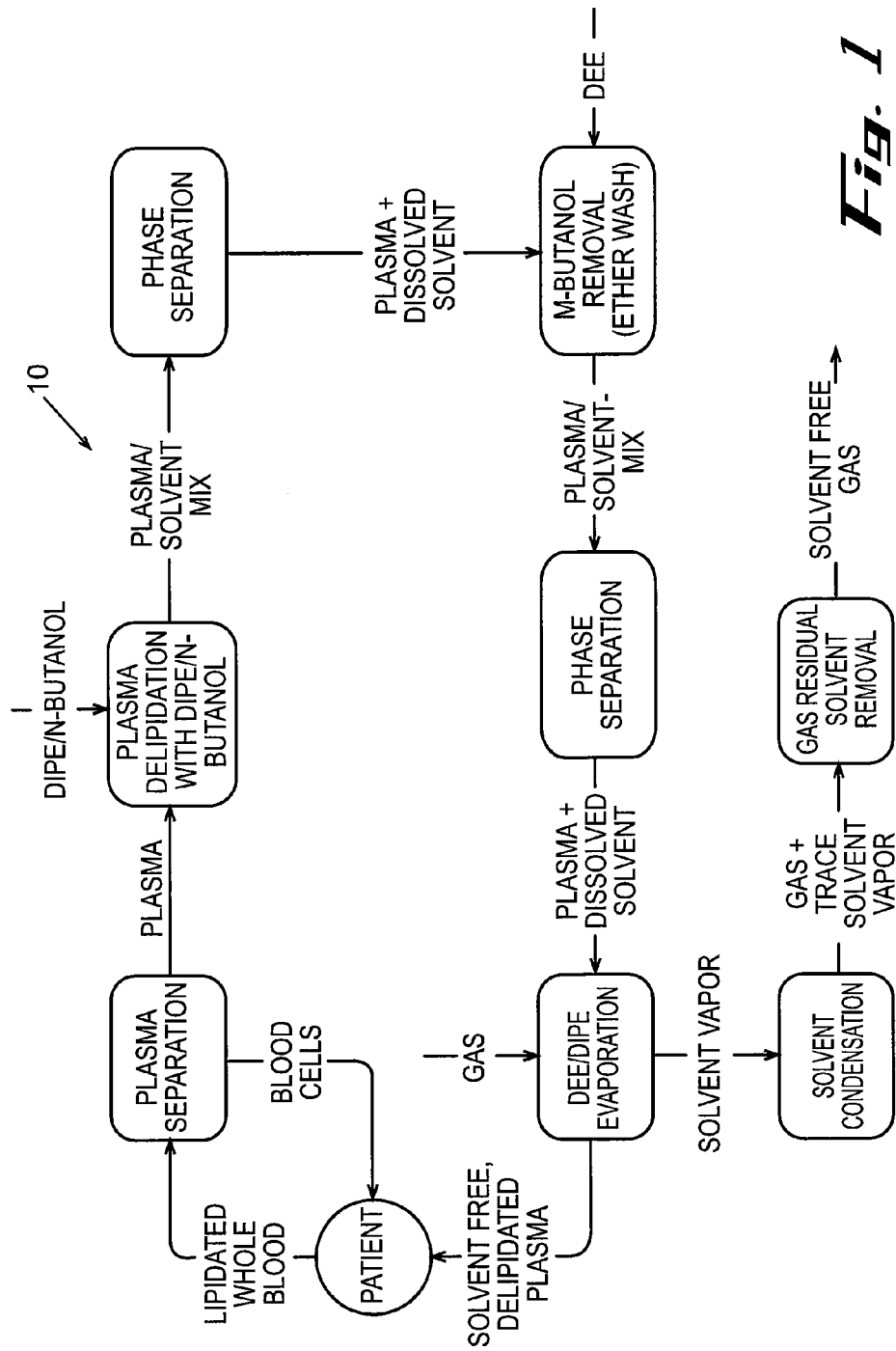
FIG. 1 is a block diagram of a delipidation method of this invention.

This invention relates to systems, apparatuses and methods useful for delipidation of fluids, including biological fluids, in animals, including humans. These systems and apparatuses can be used to treat arteriosclerosis and atherosclerotic vascular diseases by removing lipids from plasma. These systems and apparatuses can also be used to remove lipids from lipid-containing organisms, especially infectious organisms circulating within fluids of animals and humans.

I. Definitions and Solvents

A. Definitions

The term "fluid" is defined as fluids from animals or humans that contain lipids, fluids from culturing tissues and cells that contain lipids, fluids mixed with lipid-containing cells, and fluids mixed with lipid-containing organisms. For purposes of this invention, delipidation of fluids includes delipidation of cells and organisms in a fluid. Fluids include, but are not limited to: biological fluids; such as, blood, plasma, serum, lymphatic fluid, cerebrospinal fluid, peritoneal fluid, pleural fluid, pericardial fluid; various fluids of the reproductive system including, but not limited to, semen, ejaculatory fluids, follicular fluid and amniotic fluid; cell culture reagents such as, normal sera, fetal calf serum or serum derived from any animal or human; and immunological reagents such as, various preparations of antibodies and cytokines from culturing tissues and cells, fluids mixed with lipid-containing cells, and fluids containing lipid-containing organisms, such as a saline solution containing lipid-containing organisms.

The term "hollow fiber contactor" (HFC) is defined as being any conventional HFC or other HFC. Typically, HFCs have an outer body, referred to as a shell and forming a chamber, for containing a plurality of hollow fibers positioned generally parallel to a longitudinal axis of the shell. The hollow fibers are generally cylindrical tubes having small diameters formed by a permeable membrane having pores that allow certain materials pass through the membrane. The HFC allows a first material to pass through the lumens of the hollow fibers and a second material to pass through the HFC on the shell side of the hollow fibers. The first material may pass from the lumens of the hollow fibers, through the pores of the hollow fibers and into the second material on the shell side of the hollow fibers, or vice versa. The ability for the materials to pass through the pores of the hollow fibers is predicated on numerous factors,; such as pore size, pressure, flow rate, solubility, and others.

The term "drip through column" (DTC) is defined as being any conventional DTC or other DTC. A DTC functions by forming a small dispersion of one material and allowing the dispersed material to fall by gravity through another material contained in the DTC. Typically, DTCs are formed from a column that is sealed at each end. A small orifice is positioned at one end of the DTC for forming a small dispersion of a first material. The remainder of the DTC is filled with a second material through which the first material passes.

The term "lipid" is defined as any one or more of a group of fats or fat-like substances occurring in humans or animals. The fats or fat-like substances are characterized by their insolubility in water and solubility in organic solvents. The term "lipid" is known to those of ordinary skill in the art and includes, but is not limited to, complex lipid, simple lipid, triglycerides, fatty acids, glycerophospholipids (phospholipids), true fats such as esters of fatty acids, glycerol, cerebrosides, waxes, and sterols such as cholesterol and ergosterol.

The term "lipid" is also defined as including lipid-containing organisms and lipid-containing infectious agents. Such lipids may be found, for example, in a bacterial cell wall or viral envelope. Lipid-containing organisms include, but are not limited to, eukaroyotic and prokaryotic organisms, bacteria, viruses, protozoa, mold, fungi, and other lipid-containing parasites.

The term "infectious organism" means any lipid-containing infectious organism capable of causing infection. Some infectious organisms include bacteria, viruses, protozoa, parasites, fungi and mold. Some bacteria which may be treated with the method of this invention include, but are not limited to the following: *Staphylococcus; Streptococcus*, including *S. pyogenes; Enterococci; Bacillus*, including *Bacillus anthracis*, and *Lactobacillus; Listeria; Corynebacterium diphtheriae; Gardnerella* including *G. vaginalis; Nocardia; Streptomyces; Thermoactinomyces vulgaris; Treponema; Camplyobacter; Pseudomonas* including *P.aeruginosa; Legionella; Neisseria* including *N.gonorrhoeae* and *N.meningitides; Flavobacterium* including *F. meningosepticum* and *F. odoratum; Brucella; Bordetella* including *B. pertussis* and *B. bronchiseptica; Escherichia* including *E. coli; Klebsiella; Enterobacter, Serratia* including *S. marcescens* and *S. liquefaciens; Edwardsiella; Proteus* including *P. mirabilis* and *P. vulgaris; Streptobacillus; Rickettsiaceae* including *R. rickettsii; Chlamydia* including *C. psittaci* and *C. trachomatis; Mycobacterium* including *M. tuberculosis, M. intracellulare, M. fortuitum, M. laprae, M. avium, M. bovis, M. africanum, M. kansasii, M. intracellulare,* and *M. lepraemurium*; and *Nocardia*, and any other bacteria containing lipid in their membranes.

Viral infectious organisms which may be inactivated by the above system include, but are not limited to the lipid-containing viruses of the following genuses: *Alphavirus* (alphaviruses), *Rubivurus* (rubella virus), *Flavivirus* (Flaviviruses), *Pestivirus* (mucosal disease viruses), (unnamed, hepatitis C virus), *Coronavirus*, (Coronaviruses), *Torovirus*, (toroviruses), *Arteivirus*, (arteriviruses), *Paramyxovirus*, (Paramyxoviruses), *Rubulavirus* (rubulaviruses), *Morbillivirus* (morbilliviruses), *Pneumovirinae* (the pneumoviruses), *Pneumovirus* (pneumoviruses), *Vesiculovirus* (vesiculoviruses), *Lyssavirus* (lyssaviruses), *Ephemerovirus* (ephemeroviruses), *Cytorhabdovirus* (plant rhabdovirus group A), *Nucleorhabdovirus* (plant rhabdovirus group B), *Filovirus* (filoviruses), *Influenzavirus* A, B (influenza A and B viruses), *Influenza virus* C (influenza C virus), (unnamed, Thogoto-like viruses), *Bunyavirus* (bunyaviruses), *Phlebovirus* (phleboviruses), *Nairovirus* (nairoviruses), *Hantavirus* (hantaviruses), *Tospovirus* (tospoviruses), *Arenavirus* (arenaviruses), unnamed mammalian type B retroviruses, unnamed, mammalian and reptilian type C retroviruses, unnamed type D retroviruses, *Lentivirus* (lentiviruses), *Spumavirus* (spumaviruses), *Orthohepadnavirus* (hepadnaviruses of mammals), *Avihepadnavirus* (hepadnaviruses of birds), *Simplexvirus* (simplexviruses), *Varicellovirus* (varicelloviruses), *Betaherpesvirinae* (the cytomegaloviruses), *Cytomegalovirus* (cytomegaloviruses), *Muromegalovirus* (murine cytomegaloviruses), *Roseolovirus* (human herpes virus 6), *Gammaherpesvirinae* (the lymphocyte-associated herpes viruses), *Lymphocryptovirus* (Epstein-Bar-like viruses), *Rhadinovirus* (saimiri-ateles-like herpes viruses), *Orthopoxvirus* (orthopoxviruses), *Parapoxvirus* (parapoxviruses), *Avipoxvirus* (fowlpox viruses), *Capripoxvirus* (sheeppoxlike viruses), *Leporipoxvirus* (myxomaviruses), *Suipoxvirus* (swine-pox viruses), *Molluscipoxvirus* (molluscum contagiosum viruses), *Yatapoxvirus* (yabapox and tanapox viruses), Unnamed, African swine fever-like viruses, *Iridovirus* (small iridescent insect viruses), *Ranavirus* (front iridoviruses), *Lymphocystivirus* (lymphocystis viruses of fish), *Togaviridae, Flaviviridae, Coronaviridae, Enabdoviridae, Filoviridae, Paramyxoviridae, Orthomyxoviridae, Bunyaviridae, Arenaviridae, Retroviridae, Hepadnaviridae, Herpesviridae, Poxviridae*, and any other lipid-containing virus.

These viruses include the following human and animal pathogens: Ross River virus, fever virus, dengue viruses, Murray Valley encephalitis virus, tick-borne encephalitis viruses (including European and far eastern tick-borne encephalitis viruses, human coronaviruses 229-E and OC43 and others (causing the common cold, upper respiratory tract infection, probably pneumonia and possibly gastroenteritis), human parainfluenza viruses 1 and 3, mumps virus, human parainfluenza viruses 2, 4a and 4b, measles virus, human respiratory syncytial virus, rabies virus, Marburg virus, Ebola virus, influenza A viruses and influenza B viruses, *Arenaviruss*: lymphocytic choriomeningitis (LCM) virus; Lassa virus, human immunodeficiency viruses 1 and 2, or any other immunodeficiency virus, hepatitis A virus, hepatitis B virus, hepatitis C virus, Subfamily: human herpes viruses 1 and 2, herpes virus B, Epstein-Barr virus), (smallpox) virus, cowpox virus, molluscum contagiosum virus.

All protozoa containing lipid, especially in their plasma membranes, are included within the scope of the present invention. Protozoa that may be inactivated by the system and apparatus of the present invention include, but are not limited to, the following lipid-containing protozoa: *Trypanosoma brucei, Trypanosoma gambiense, Trypanosoma cruzi, Leishmania donovani, Leishmania vianni, Leishmania tropica, Giardia lamblia, Giardia intestinalis, Trichomonas vaginalis, Entamoeba histolytica, Entamoeba coli, Entamoeba hartmanni, Naegleria* species, *Acanthamoeba* species, *Plasmodium falciparum, Plasmodium vivax, Plasmodium malariae, Plasmodium ovale, Toxoplasma gondii, Cryptosporidium parvum, Cryptosporidium muris, Isospora belli, Cyclospora cayetansis, Balantidium* species, *Babesia bovis, Babesia, microti, Babesia divergens, Encephalitozoon intestinalis, Pleistophora* species, *Nosema ocularum, Vittaforma corneae, Septata intestinalis, Enterocytozoon, Dientamoeba fragilis, Blastocystis* species, *Sarcocystis* species, *Pneumocystis carinii, Microsporidium africanum, Microsporidium ceylonensis, Eimeria acervulina, Eimeria maxima, Eimeria tenella* and *Neospora caninum*. It is to be understood that the present invention is not limited to the protozoa provided in the list above.

A preferred protozoa treated with the method of the present invention is Coccidia, which includes *Isospora* species, *Cryptosporidium* species, *Cyclospora* species, *Toxoplasma* species, *Sarcocystis* species, *Neospora* species, and *Eimeria* species. These coccidian parasites cause intestinal disease, lymphadenopathy, encephalitis, myocarditis, and pneumonitis.

The terms "protozoal infection" or "infectious disease" mean diseases caused by protozoal infectious organisms. The diseases include, but are not limited to, African sleeping sickness, Chagas' disease, Leishmaniasis, Giardiasis, Trichomoniasis, amebiasis, primary amebic encephalitis, granulomatous amebic encephalitis, malaria, Toxoplasmosis, Cryptosporidiosis, Isosporiasis, Cyclosporiasis, Balantidiasis, Babesiosis, microsporidiosis, Dientamoeba fragilis infection, Blastocystis hominis infection, Sarcosporidiosis, pneumonia, and coccidiosis. A preferred protozoal infection treated with the method of the present invention is Coccidiosis, which is caused by *Isospora* species, *Cryptosporidium* species, *Cyclospora* species, *Toxoplasma* species, *Sarcocystis* species, *Neospora* species, and *Eimeria* species. These coccidian parasites cause human intestinal disease, lymphadenopathy, encephalitis, myocarditis, and pneumonitis. These coccidian parasites also cause disease in animals, including cattle, dogs, cats, and birds. Avians, and chickens, turkeys and quail in particular, are affected by Coccidiosis, especially by *Eimeria* species such as *E. acervulina, E. maxima, E. necatrix, E. bruneti, E. mitis, E. praecox* and *E. tenella*.

The term "continuous" refers to the process of delipidating a fluid, such as plasma, while the animal or human remains connected to an apparatus for delipidating the fluid. Additionally, "continuous" refers to the internal process of the lipid removal system, wherein the fluid continually flows within the lipid removal system from subsystem to subsystem.

The term "batch" refers to the process of delipidating a fluid, such as plasma, without returning or passing the delipidated fluid directly to the animal or human during the delipidation process. Rather, the delipidated fluid is stored. Additionally, "batch" refers to the internal process of the lipid removal machine, wherein the fluid does not continually flow within the lipid removal system from subsystem to subsystem.

The term "delipidation" refers to the process of removing lipids from a fluid or from a lipid-containing organism.

The term "first extraction solvent" is defined as one or more solvents used in the initial stage subsystem of extracting lipids from a fluid. The first extraction solvent enters the fluid and remains in the fluid until removed by other subsystems. Suitable extraction solvents include solvents that extract or dissolve lipids, including, but not limited to, alcohols, phenols, hydrocarbons, amines, ethers, esters, halohydrocarbons, halocarbons, and combinations thereof. Preferred first extraction solvents are combinations of alcohols and ethers, which include, but are not limited to n-butanol, di-isopropyl ether (DiPE), which is also referred to as isopropyl ether, diethyl ether (DEE), which is also referred to as ethyl ether, sevoflourane, perfluorocyclohexanes, trifluoroethane, isoflurane, cyclofluorohexanol and combinations thereof.

The term "second extraction solvent" is defined as one or more solvents that facilitate removal of at least a portion of the first extraction solvent. Suitable second extraction solvents include any solvent that facilitates removal of the first extraction solvent mixed with or exposed to the fluid containing lipids or lipid-containing organisms, or both. Second extraction solvents include any solvent that facilitates removal of the first extraction solvent including, but not limited to, ethers, alcohols, phenols, hydrocarbons, amines, esters, halohydrocarbons, halocarbons, and combinations thereof. Preferred second extraction solvents include an ether, such as diethyl ether, which facilitates removal of lower order alcohols, such as n-butanol, from the fluid.

The term "patient" refers to animals and humans, which may be either a fluid source or a recipient of delipidated fluid or delipidated organisms.

B. Solvents

Numerous organic solvents may be used in the method of this invention for removal of lipid from fluids and from lipid-containing organisms, especially infectious organisms, provided that the solvents or combinations thereof are effective in solubilizing lipids. Suitable solvents comprise mixtures of hydrocarbons, ethers, alcohols, phenols, esters, halohydrocarbons, halocarbons and amines. Other solvents which may be used with this invention include amines and mixtures of amines. Preferred solvents are combinations of alcohols and ethers. Another preferred solvent comprises an ether or combinations of ethers. It is preferred that the solvent or combination of solvents has a relatively low boiling point to facilitate removal via a combination of vacuum and possibly heat applications.

Examples of suitable amines for use in removal of lipid from lipid-containing organisms are those which are substantially water immiscible. Typical amines are aliphatic amines having a carbon chain of at least 6 carbon atoms. A non-limiting example of such an amine is $C_6H_{13}NH_2$. Another suitable amine is perfluorotributyl amine.

The alcohols which are preferred for use in this invention, when used alone, include those alcohols that are not appreciably miscible with plasma or other fluids. Such alcohols include, but are not limited to, straight chain and branched chain alcohols, including pentanols, hexanols, heptanols, octanols, and alcohols containing higher numbers of carbons. Halogenated alcohols may be employed, including, but not limited to, heptafluoro-butanol.

When alcohols are used in combination with another solvent, for example, an ether, a hydrocarbon, an amine, or a combination thereof, $C_1$–$C_8$ containing alcohols may be used. Preferred alcohols for use in combination with another solvent include $C_4$–$C_8$ containing alcohols. Accordingly, preferred alcohols are butanols, pentanols, hexanols, such as 1-hexanol, heptanols, octanols, and ethanols, and iso forms thereof. Particularly preferred are the butanols (1-butanol and 2-butanol). As stated above, the most preferred alcohol is the $C_4$ alcohol, butanol. The specific choice of alcohol will depend on the second solvent employed. In a preferred embodiment, lower alcohols are combined with lower ethers.

Ethers, used alone, or in combination with other solvents, preferably alcohols, are another preferred solvent for use in the method of the present invention. Particularly preferred are the $C_4$–$C_8$ containing-ethers, including but not limited to, diethyl ether, and propyl ethers, including but not limited to di-isopropyl ether. Asymmetrical ethers and halogenated ethers may also be employed. Also useful in the present invention are combinations of ethers, such as di-isopropyl ether and diethyl ether. When ethers and alcohols are used in combination as a first solvent for contacting the fluid containing lipids or lipid-containing organisms, or both, any combination of alcohol and ether may be used provided the combination is effective to partially or completely remove lipids from the fluid or the lipid-containing organism. In one embodiment, lipids are removed from the viral envelope or bacterial cell wall of the infectious organism, which reduces the infectivity of the infectious organism.

When alcohols and ether are combined as a first extraction solvent for removing lipids from a fluid containing lipids or lipid-containing organisms, or both, preferred ratios of alcohol to ether in this solvent are about 0.01%–60% alcohol to about 40%–99.99% of ether, with a preferred ratio of about 10%–50% of alcohol with about 50%–90% of ether, with a most preferred ratio of about 20%–45% alcohol and about 55%–80% ether. An especially preferred combination of alcohol and ether is the combination of butanol and di-isopropyl ether. Another especially preferred combination of alcohol and ether is the combination of butanol with diethyl ether.

When butanol and di-isopropyl ether are combined as a first extraction solvent for removing lipids from a fluid containing lipids or lipid-containing organisms, or both, contained in a fluid, preferred ratios of butanol to di-isopropyl ether in this solvent are about 0.01%–60% butanol to about 40%–99.99% of di-isopropyl ether, with a preferred ratio of about 10%–50% of butanol with about 50%–90% of di-isopropyl ether, with a most preferred ratio of about 20%–45% butanol and about 55%–80% di-isopropyl ether. The most preferred ratio of butanol and di-isopropyl ether is about 40% butanol and about 60% di-isopropyl ether.

When butanol is used in combination with diethyl ether in a first extraction solvent, preferred ratios of butanol to diethyl ether in this combination are about 0.01%–60% butanol to about 40%–99.99% diethyl ether, with a preferred ratio of about 10%–50% butanol with about 50%–90% diethyl ether, with a most preferred ratio of about 20%–45% butanol and about 55%–80% diethyl ether. The most preferred ratio of butanol and diethyl ether in a first solvent is about 40% butanol and about 60% diethyl ether.

Hydrocarbons in their liquid form dissolve compounds of low polarity such as the lipids in fluids and lipids found in membranes of organisms. Hydrocarbons which are liquid at about 37° C. are effective in disrupting a lipid membrane of an infectious organism. Accordingly, hydrocarbons comprise any substantially water immiscible hydrocarbon which is liquid at about 37° C. Suitable hydrocarbons include, but are not limited to, the following: $C_5$ to $C_{20}$ aliphatic hydrocarbons such as petroleum ether, hexane, heptane, and octane; haloaliphatic hydrocarbons such as chloroform, trifluoroethane, 1,1,2-trichloro-1,2,2-trifluoroethane, 1,1,1-trichloroethane, trichloroethylene, tetrachloroethylene dichloromethane and carbon tetrachloride; thioaliphatic hydrocarbons; perfluorocarbons, such as perfluorocyclohexane, perfluorohexane, perfluoromethylcyclohexane, and perfluorodimethylcyclohexane; fluroethers such as sevoflurane; each of which may be linear, branched or cyclic, saturated or unsaturated; aromatic hydrocarbons such as benzene; alkylarenes such as toluene, haloarenes, haloalkylarenes and thioarenes. Other suitable solvents may also include: saturated or unsaturated heterocyclic compounds such as water insoluble derivatives of pyridine and aliphatic, thio or halo derivatives thereof; and perfluorooctyl bromide. Another suitable solvent is perfluorodecalin.

II. Introduction

For purposes of explanation, the removal of lipids from plasma, termed delipidation, is discussed here in detail. However, this is not meant to limit the application of the invention solely to delipidation of plasma. Rather, the same principles and process apply to other fluids and to removal of lipids from lipid-containing organisms. The delipidation system 10 of this invention, as shown in FIG. 1, is capable of removing at least a portion of a total concentration of lipids from a fluid containing lipids or from lipid-containing organisms. In one embodiment, delipidation system 10 receives fluid from a patient, or other source, removes lipid contained in the fluid, and returns the delipidated fluid to the patient, or other source. The delipidation system 10 of this invention may be used as a continuous system, by returning fluid to a patient immediately after lipids have been removed or as a batch system, which removes lipids from a fluid but does not return the fluids immediately to the patient. Instead, the processed fluid can be stored and administered at a later time.

In general, the delipidation system 10 is comprised of various combinations of subsystems that perform the initial, intermediate, and final phases of a delipidation method. The initial phase includes removing lipids from a fluid containing lipids or lipid-containing organisms, or both, using a first extraction solvent. In one embodiment, the first extraction solvent is composed of a mixture of two solvents. The intermediate phase includes washing the fluid received from the initial phase to remove at least a portion of the first extraction solvent. The wash may be conducted using at least one second extraction solvent. The intermediate phase may also remove a portion of lipids that remain attached to the fluid. The final phase is the removal of the first and second extraction solvents from the fluid to an acceptable level, such as below about 10 parts per million (ppm) or below about 50 milligrams of solvent per 3.5 liters of fluid, for administering the fluid to a patient without causing undesirable consequences. Although the following paragraphs primarily describe removal of lipids from fluids, it is understood that the same discussion applies to removal of lipids from lipid-containing organisms.

Each of these phases may be performed using the same device or devices or any combination of devices. For instance, each phase may be conducted using at least one of the following devices including, but not limited to, an HFC, a DTC, an in-line static mixer, a depth filter, a vortexer, a centrifuge, or end-over-end rotation of a sealed container, or any combination of these devices. Each of these phases may be completed using an initial phase subsystem 12, an intermediate phase subsystem 14, and a final phase subsystem 16, as shown schematically in FIGS. 2, 9 and 10. Each phase of the delipidation process may be accomplished using numerous combinations of components. The initial phase subsystem 12 removes lipids from a fluid containing lipids or lipid-containing organisms, or both, such as plasma, by placing a first extraction solvent in contact with the fluid.

In the first phase subsystem 12, at least a portion of the total concentration of lipids in the fluids is removed and, in at least one embodiment, a substantial portion of the lipids contained in a fluid is removed. In addition, a portion of the first extraction solvent mixes with the fluid forming a first mixture that is sent to the intermediate phase subsystem. This may be accomplished using at least one of the following devices including, but not limited to, an HFC, a DTC, an in-line static mixer, end-over-end rotation of a sealed container, at least one depth filter, a vortexer, or a centrifuge, or any combination of these devices.

The intermediate phase subsystem 14 receives the first mixture of the fluid and first extraction solvent from initial phase subsystem 12 and completes the delipidation process by removing at least a portion of the first extraction solvent and lipids from the fluid using a second extraction solvent. During this process, a portion of the second extraction solvent may mix with the first mixture of fluid and first extraction solvent to form a second mixture. As with the first phase subsystem 12, this may accomplished in many ways. For instance, the intermediate phase subsystem 12 may be composed of at least one of the following devices including, but not limited to, an HFC, a DTC, an in-line static mixer, end-over-end rotation of a sealed container, at least one depth filter, a vortexer, or a centrifuge, or any combination of these devices. This second mixture is then sent to the final phase subsystem 16.

The final phase subsystem 16 receives the second mixture of fluid and the first and second extraction solvents from intermediate phase subsystem 14 and removes at least a portion of the residual first extraction solvent and a majority of the second extraction solvent from the fluid using an inert gas, such as, but not limited to, air, nitrogen or other inert gas, or a mineral oil, or other material. The delipidated plasma is then in a condition to be returned to a patient or stored for administration to another patient. The final phase subsystem 16 likewise may comprise numerous configurations. For instance, in some embodiments, the final phase subsystem 16 may be composed of at least one HFC. In other embodiments, the final phase subsystem 16 may be composed of at least two HFCs in parallel or series configuration. In certain embodiments, the final phase subsystem 16 can remove sufficient amounts of the first and second extraction solvents to safely administer the fluid to a patient after the second mixture has passed through the system only one time. In other embodiments, the second mixture must be sent through the final phase subsystem multiple times before the concentration of first and second extraction solvents is reduced to an acceptable level for administration of the delipidated fluid to the patient.

In another embodiment, each phase of the delipidation method may be performed using a single device, such as an HFC or other such device. For instance, each phase may be conducted using a single HFC for conducting initial, intermediate, and final phases of the delipidation method. The HFC may be flushed or reoriented between each phase of the delipidation as well. In yet another embodiment, the initial phase and the intermediate phase may be conducted using the same device or devices that may be formed from the devices listed immediately above or other devices. For instance, the apparatus may include, but is not limited to, an in-line static mixer, a vortexer, or a HFC, or any combination thereof.

This process is shown schematically in FIG. 1 as being adapted to remove lipids from plasma or from lipid-containing organisms, or both. For instance, whole blood is drawn from a patient using conventional procedures and is subjected to a conventional plasma separation process using, for instance, cellular separation systems that may be composed of, but are not limited to, apheresis and plasmapheresis systems, such as SPECTRA and TRIMA manufactured by Cobe BCT, Gambro BCT, Lakewood, Colo.; AUTOPHERESIS-C manufactured by Baxter Healthcare Corporation, Deerfield, Ill.; or AS104 manufactured by Fresenius, Berlin, Germany. In another embodiment, blood is combined with an anticoagulant, such as sodium citrate, and centrifuged at forces approximately equal to 2,000 times gravity. The red blood cells are then aspirated from the plasma. The plasma separation process collects plasma and returns the blood cells to the patient. The plasma is then subjected to the lipid removal process of this invention, which is described in detail below.

III. The Delipidation System

As discussed above, the delipidation system 10 may be composed of numerous designs. In one embodiment, delipidation system 10 is composed of at least three subsystems. These subsystems may be composed of numerous components to accomplish the objectives described above. In another embodiment, a single system may be used to perform two or more phases of the delipidation method. Set forth below are numerous embodiments formed from different components that are capable of achieving these objectives. These embodiments are described to teach the invention and are not meant to limit the scope of the invention. Rather, each embodiment is but one of many possible configurations that can be used to accomplish the objectives described above.

Suitable materials for use in any of the apparatus components as described herein include materials that are biocompatible, approved for medical applications that involve contact with internal body fluids, and in compliance with U.S. PV1 or ISO 10993 standards. Further, the materials should not substantially degrade, from, for instance, exposure to the solvents used in the present invention, during at least a single use. The materials should typically be sterilizable either by radiation or ethylene oxide (EtO) sterilization. Such suitable materials should be capable of being formed into objects using conventional processes, such as, but not limited to, extrusion, injection molding and others. Materials meeting these requirements include, but are not limited to, nylon, polypropylene, polycarbonate, acrylic, polysulphone, polyvinylidene fluoride (PVDF), fluoroelastomers such as VITON, available from DuPont Dow Elastomers L.L.C., thermoplastic elastomers such as SANTOPRENE, available from Monsanto, polyurethane, polyvinyl chloride (PVC), polytetrafluoroethylene (PTFE), polyphenylene ether (PFE), perfluoroalkoxy copolymer (PFA), which is available as TEFLON PFA from E.I. du Pont de Nemours and Company, and combinations thereof.

The valves used in each embodiment may be, but are not limited to, pinch, globe, ball, gate or other conventional valves. Thus, the invention is not limited to a valve having a particular style. Further, the components of each system described below may be coupled directly together or coupled together using conduits that may be composed of flexible or rigid pipe, tubing or other such devices known to those of ordinary skill in the art.

A. First Embodiment

1. Initial Phase Subsystem

Figure 2:
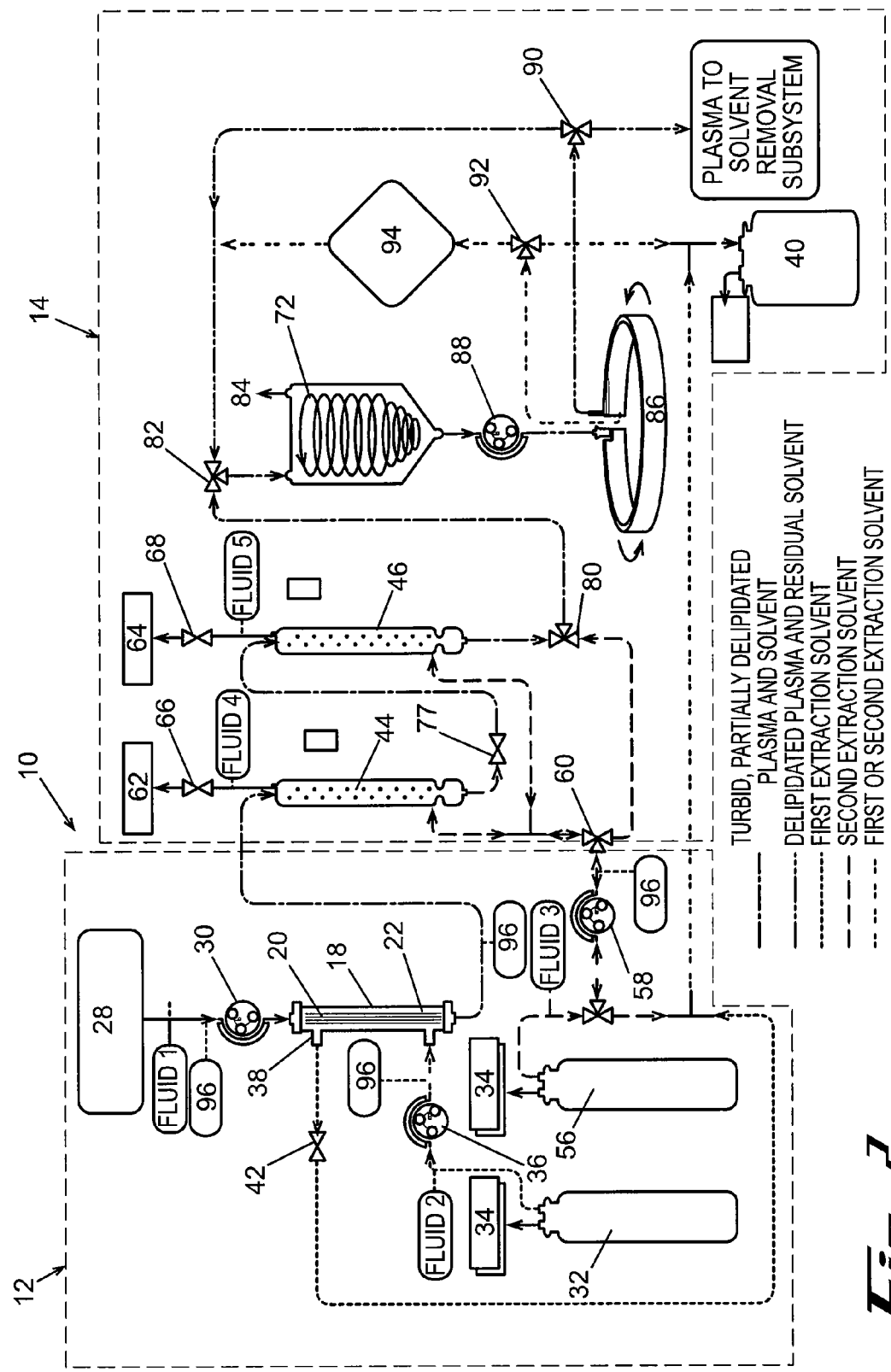
FIG. 2 is a schematic diagram of a first embodiment of this invention showing an initial phase subsystem and an intermediate phase subsystem.
Figure 9:
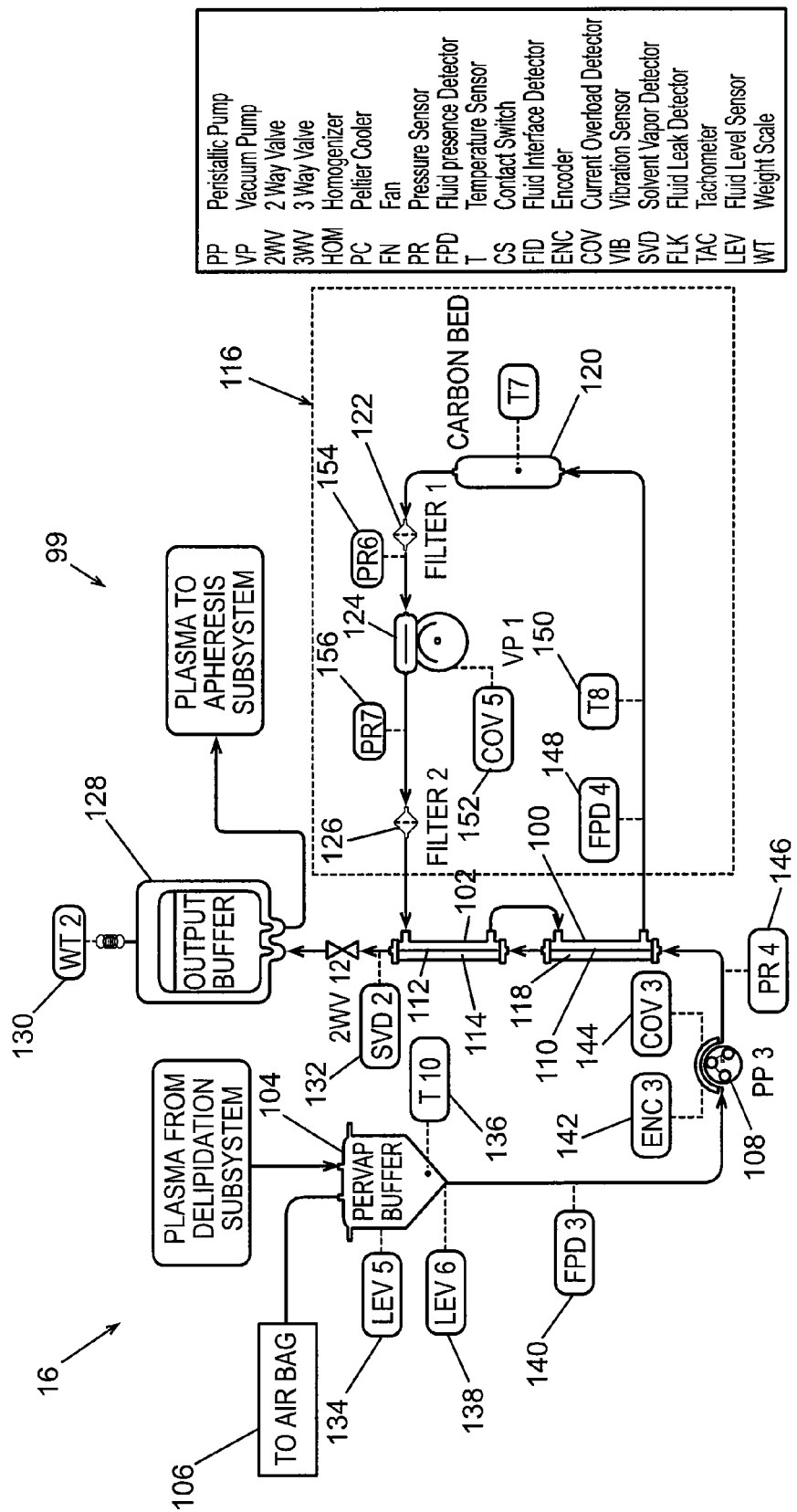
FIG. 9 is a schematic diagram of an embodiment of a final phase subsystem for reducing the concentration of first and second extraction solvents in a delipidated fluid.
Figure 10:
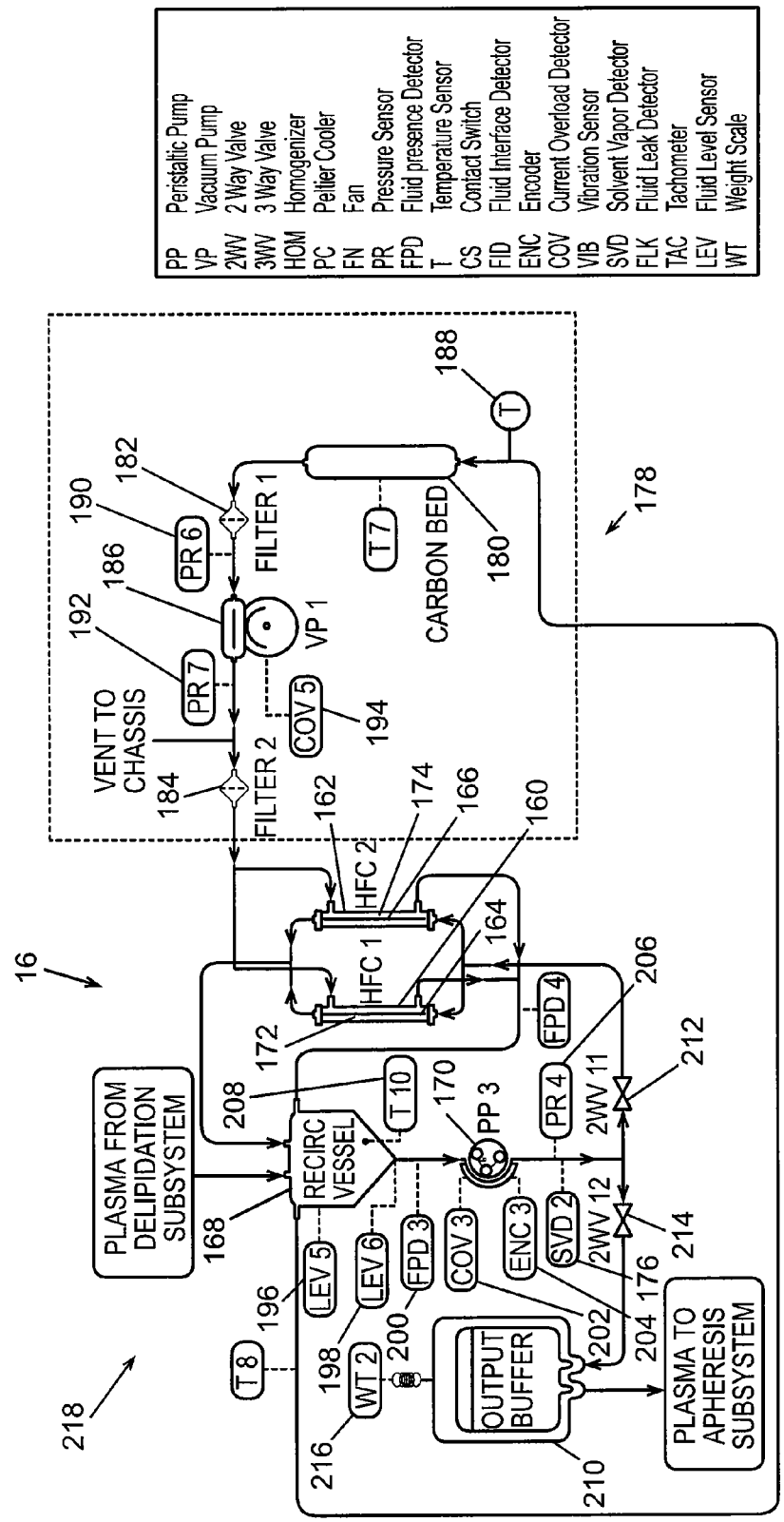
FIG. 10 is a schematic diagram of another embodiment of the final phase subsystem for reducing the concentration of first and second extraction solvents in the delipidated fluid.

FIG. 2 shows a delipidation system 10 composed of an initial phase subsystem 12 and an intermediate phase subsystem 14, and FIGS. 9 and 10 show two embodiments of a final phase subsystem 16. Referring to FIG. 2, initial phase subsystem 12 is formed with a HFC 18. While the embodiment depicted in FIG. 2, shows a single HFC, the initial phase subsystem 12 is not limited to a single HFC but may include additional HFCs. The number of HFCs used in each subsystem may be dictated by the amount of lipid removal desired. The number and size of the HFCs are a function of the flow rate of fluids or gases within the lumens of the hollow fibers and on the shell side of the hollow fibers of the HFC, the porosity of the hollow fibers, and the amount of surface area of the hollow fiber membrane. Adjusting one of these factors requires the other factors be changed in order to yield the same output at the same rate. Additionally, patients having higher initial levels of lipids may require more HFCs to be used to obtain the desired degree of lipid removal.

Figure 3:
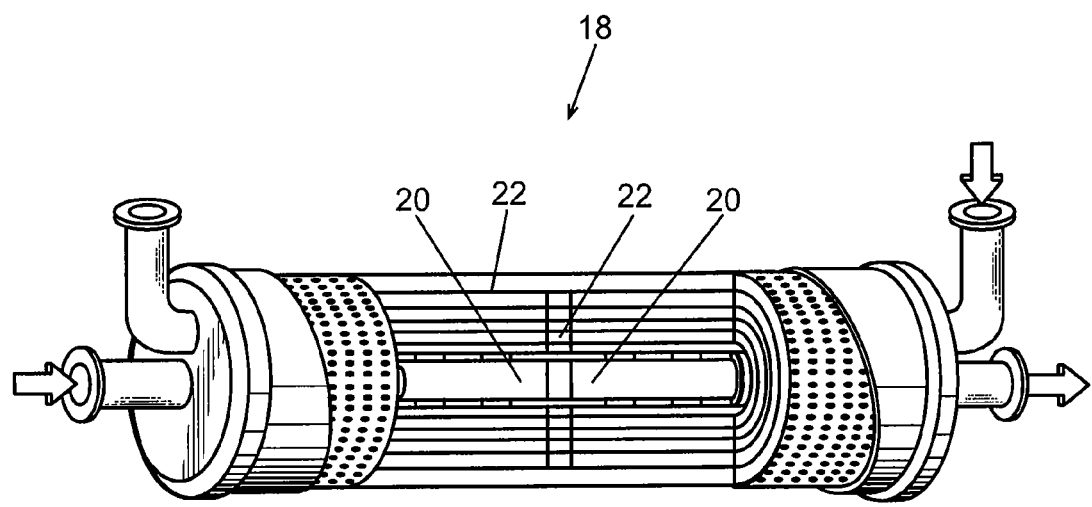
FIG. 3 is a perspective view of a HFC usable to practice this invention with a partial cut away section.
Figure 4:
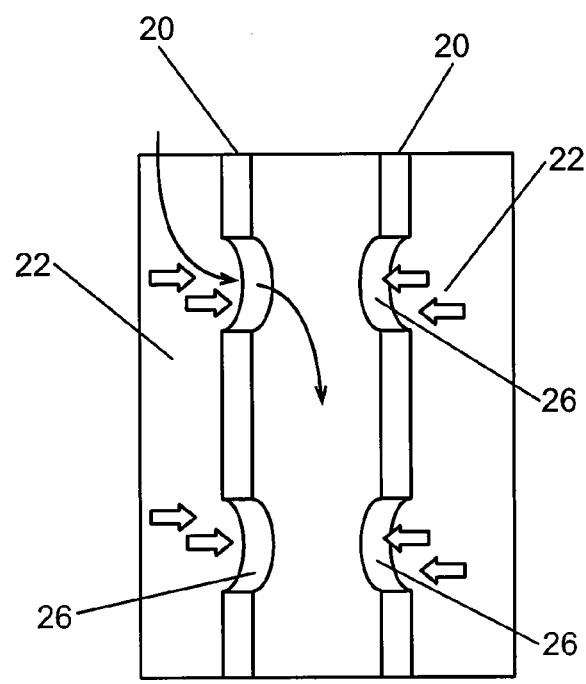
FIG. 4 is cross-sectional view of a portion of a hollow fiber membrane of the HFC shown in FIG. 3.

HFC 18, as shown in more detail in FIG. 3, may be formed from a generally hollow cylindrical body having a diameter ranging between about 1½ inches to about 4 inches that forms a chamber 22 containing a plurality of hollow fibers 20. Hollow fibers 20 are tubes having small diameters, such as between about 0.2 mm and about 1.0 mm, and typically number between about 3,000 and about 5,000. However, hollow fibers 20 may number one or more. Chamber 22 is formed by the inside surface of the cylindrical body of HFC 18 and the outside surfaces of hollow fibers 20. Chamber 22 is commonly referred to as the shell side of the hollow fibers 20. Each hollow fiber 20, as shown in FIG. 4, is a cylindrical tube having a small diameter and is formed from a membrane having pores 26 sized to allow gases and liquids to pass through the membrane. Pores 26 may have a diameter within the range of between about 5 kilodaltons and about 500 kilodaltons or between about 3 nanometers and about 300 nanometers. Varying the size of pores 26 can allow either more or less materials to pass through pores 26. Hollow fibers 20 are positioned in HFC 18 so that their longitudinal axes are generally parallel to the longitudinal axis of the HFC 18. Pores 26 need only be large enough to allow the first and second extraction solvents and a gas to diffuse through pores 26 and for lipids to diffuse through pores 26 and into the solvents.

While not being bound by the following statements, the following discussion is a possible explanation of the operation of the system at the pores 26 of the hollow fibers. The hollow fibers 20 may be formed of either hydrophobic or hydrophilic materials. If hollow fibers 20 formed from a hydrophobic material are used, the solvent fills pores 26 and an interface forms between the solvent in pores 26 and the fluid that remains in the lumens. The solvent diffuses across the interface into the fluid, but there is minimal mixing of the fluid and the solvent. Thus, there exists very little possibility of an emulsion forming. The lipids that may have been solubilized by the action of the solvents diffuse into the solvent in the pores 26 at the interface. The lipids continue to diffuse through pores 26 until the lipids are swept away by the solvent flowing through HFC 18 on the shell side 22 of the lumens. If a hydrophilic material is used to form hollow fibers 20, pores 26 fill with fluid, and the solvent does not fill pores 26. The lipids then diffuse through pores 26.

The preferred material is a hydrophobic material because the highest transport rate is achieved when pores 26 are filled with the material having the highest solubility for the material desired to be passed through pores 26. In this case, lipids are more soluble in the solvents described above than in the fluid.

The flow rate of the fluid and first extraction solvent through HFC 18 dictates the required amount of permeable surface area on hollow fibers 20. For instance, the slower the flow rate, the smaller the surface area required, and, conversely, the faster the flow rate, the larger the surface area required. This is dictated by a mass transport formula. The formula below illustrates the situation for a soluble gas:

$$Q_1(C_{in} - C_{out}) = K_1 A_m \Delta C_{lm} = K_1 A_m \frac{\left(C_{in} - \frac{P_{out}}{H}\right) - \left(C_{out} - \frac{P_{in}}{H}\right)}{\ln \frac{C_{in} - \frac{P_{out}}{H}}{C_{out} - \frac{P_{out}}{H}}}$$

where $C_{out}$ represents the liquid phase concentration (output), $C_{in}$ represent the liquid phase concentration (input), $K_1$ represents the overall mass transport coefficient, $A_m$ represents the total membrane contact area, $Q_1$ represents the liquid flow rate, H represents the Henry's Law coefficient and P represents the gas phase partial pressure. If $P_{in}$ and $P_{out}$ are small in magnitude and/or H is large, the terms P and H are negligible and the first equation simplifies to:

$$C_{out} = C_{in} \ln\left(-\frac{K_1 A_m}{Q_1}\right).$$

Examples of commercially available HFCs are the CEL-GARD mini model no. G471, G476, or G478, available from CelGard, Charlotte, N.C., and the Spectrum MINI-KROS model no. M21S-600-01N, available from Spectrum Laboratories, Inc., Rancho Dominguez, Calif.

Initial phase subsystem 12 is configured to allow a fluid containing lipids or lipid-containing organisms, or both, to flow through lumens of hollow fibers 20 of HFC 18 and to allow a first extraction solvent to flow through chamber 22 on the shell side of HFC 18, or vice versa. In one embodiment, the fluid flows through the lumens of hollow fibers 20 in the same general direction as the first extraction solvent. However, in another embodiment, the fluid flows generally opposite to the direction of flow of the first extraction solvent in the shell side 22, referred to as countercurrent flow. Pores 26 of hollow fibers 20 allow the first extraction solvent to cross the hollow fiber membrane 20 and to contact the fluid. The first extraction solvent separates the lipids contained in the fluids. If the fluid is a plasma taken from blood, the first extraction solvent separates the lipids from the proteins in the plasma. At least a portion of the separated lipids diffuse through pores 26 into the shell side 22 of hollow fibers 20 of HFC 18 and are deposited into waste receptacle 40. In certain embodiments, a portion of the separated lipids do not diffuse through pores 26 but attach to the inside surface of the hollow fiber membrane 20. Thus, initial phase subsystem 12 separates at least a portion of the lipids contained in the fluid and in certain embodiments separates a significant amount of the lipids. While a portion of the first extraction solvent returns to the shell side 22 of the HFC across hollow fiber membrane 20, a portion of the first extraction solvent remains mixed with the fluid in the lumens of hollow fibers 20 forming a first mixture.

A fluid containing lipids or lipid-containing organisms, or both, is supplied to HFC 18 from a fluid source 28, which may be a container, an apheresis system, such as any one of the previously mentioned systems, or other source. The fluid may be administered to the lumens of hollow fibers 20 of HFC 18 using gravity, a vacuum, a pump 30, or other means. Pump 30 may be a peristaltic pump, such as MASTERFLEX L/S model number 07523-40 available from Cole Parmer Instrument Company, Vernon Hills, Ill., or other pumps not having vanes that contact the fluid being pumped.

The shell side 22 of HFC 18 is coupled to a first extraction solvent source 32, which supplies a first extraction solvent to HFC 18. First extraction solvent source 32 includes vent 34 for relieving pressure and preventing unsafe conditions. The first extraction solvent may be administered to shell side 22 of the HFC 18 using gravity, a vacuum, a pump 36, which may be a peristaltic pump or other pump, or other means. HFC 18 includes a waste port 38 on the shell side 22 of HFC 18 for removing the first extraction solvent. The waste port 38 is in fluid communication with a waste receptacle 40, which may be a container or other device for containing the first extraction solvent. A valve 42 may be coupled between waste port 38 and waste receptacle 40 for controlling the discharge of the first extraction solvent from the shell side 22 of HFC 18. The lumens of hollow fibers 20 of HFC 18 are coupled to the intermediate phase subsystem 14.

2. Intermediate Phase Subsystem

Figure 5:
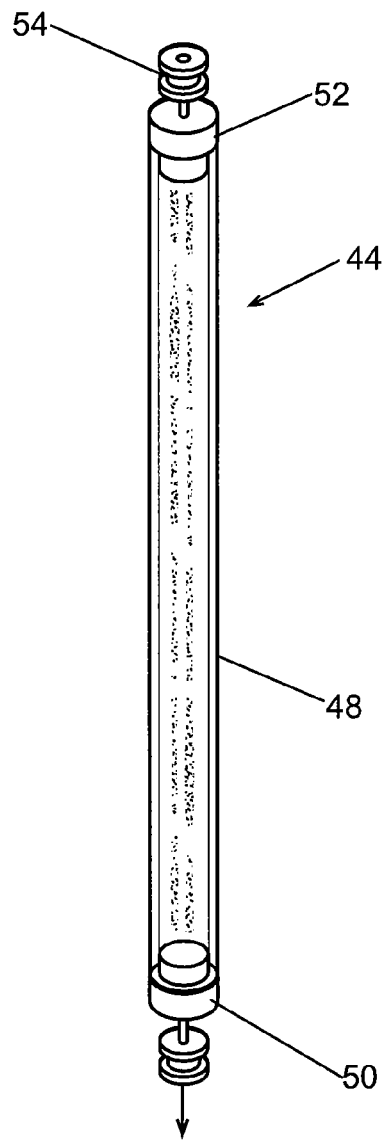
FIG. 5 depicts an example of a DTC usable to practice this invention.

The intermediate phase subsystem 14 is composed of at least one DTC and may be composed of two DTCs 44 and 46 in series, as shown in FIG. 2, or in parallel (not shown). The input port of DTC 44 is in fluid communication with the lumens of hollow fibers 20 of HFC 18 and receives the first mixture from HFC 18. A DTC, such as DTC 44 and 46, is typically composed of a hollow cylindrical tube or column 48 having a cap 50 and 52 at each end, as shown in FIG. 5. The DTC includes an injection device 54, which is typically a small gauge needle, for injecting a fine dispersion of the first mixture into the hollow cylinder forming the DTC. The dispersed first mixture falls by gravity through the second extraction solvent. As the first mixture falls through the second extraction solvent, the second extraction solvent separates a portion of the first extraction solvent from the fluid. For instance, in one embodiment, the first extraction solvent is a mixture of n-butanol and DiPE, and the second extraction solvent is DiPE. The second extraction solvent removes a portion of the n-butanol and may remove a substantial amount of the n-butanol. The second extraction solvent may also separate lipids remaining in the fluid. The lipids extracted from the first mixture are dissolved in the second extraction solvent, and the fluid eventually comes to rest on cap 50 of DTC 44. At this point, the fluid is composed of a mixture of the first and second extraction solvents and is referred to as a second mixture.

DTCs 44 and 46 are in fluid communication with a second extraction solvent container 56, which contains the second extraction solvent, as shown in FIG. 2. The second extraction solvent can flow from the second extraction solvent container 56 to DTCs 44 and 46 by gravity, by pump 58, which may be a peristaltic pump or other pump, or by other means. A three-way valve 60 controls the flow of the second extraction solvent into DTC 44. Vents 62 and 64 are coupled to DTCs 44 and 46, respectively, and for safe operation and are controlled using valves 66 and 68. Valve 70 controls the flow of the second mixture, composed of the fluid and first and second extraction solvents, between DTC 44 and DTC 46. Valves 80 and 82 control the flow of the second mixture from DTC 46 to the remainder of intermediate phase subsystem 14.

Figure 6:
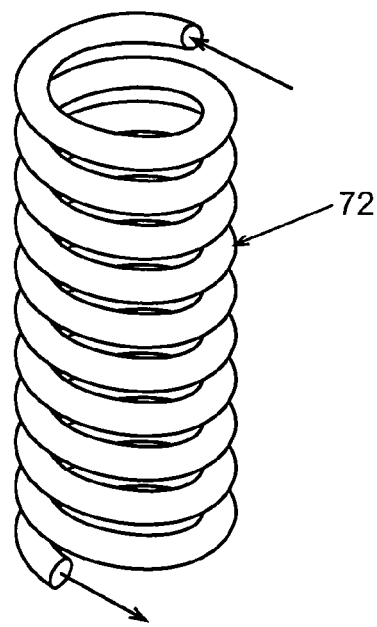
FIG. 6 is a schematicized perspective view of a continuous vortexer usable to practice this invention.
Figure 7:
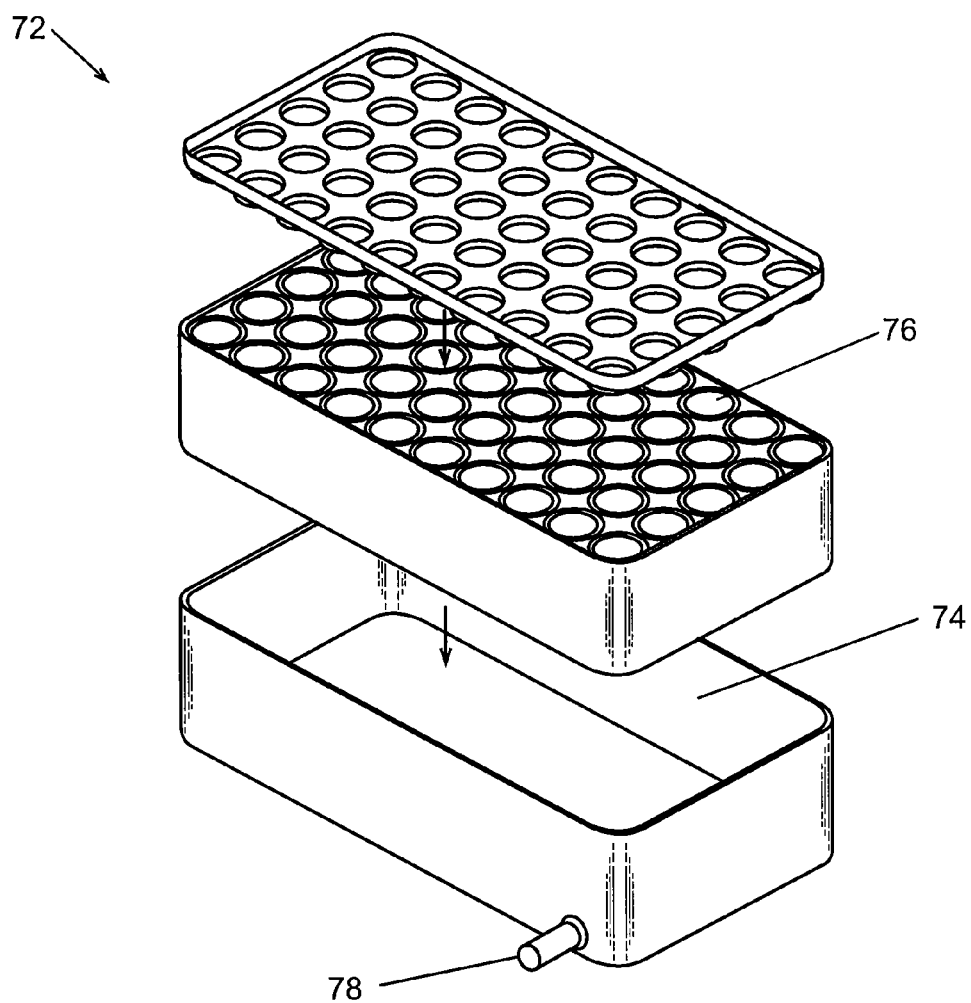
FIG. 7 is a schematicized perspective view of a batch vortexer usable to practice this invention.

The intermediate phase subsystem 14 may also include a vortexer 72 for mixing the first and second extraction solvents with the fluid. Vortexer 72 may be composed of many designs, such as a continuous vortexer shown in FIG. 6 or a batch vortexer shown in FIG. 7. Vortexer 72 also includes a vent 84 for safe operation. Referring to FIG. 6, a continuous vortexer is generally composed of a cylindrical tube configured in a spiral formation. This configuration creates vortices within a fluid flowing through the cylindrical tube and is capable of processing the fluid in a continuous fashion as the fluid flows through vortexer 72. The vortexer 72 is operated using external vibration. An alternative design is a batch vortexer 72, as shown in FIG. 7. The batch vortexer 72 is composed of housing 74 that contains a plurality of vortex chambers 76. The batch vortexer 72 is capable of receiving a fluid and a solvent through inlet port 78. The batch vortexer 72 is externally vibrated to create vortices within each vortex chamber 76. The non-rotating vortexer 72 is advantageous because of its simple design is less expensive than more complicated designs. Thus, it may be used more efficiently than other devices in a disposable system. Further, vortexer 72 does not contain any bushings, bearings or moving parts that are subject to failure.

Figure 8:
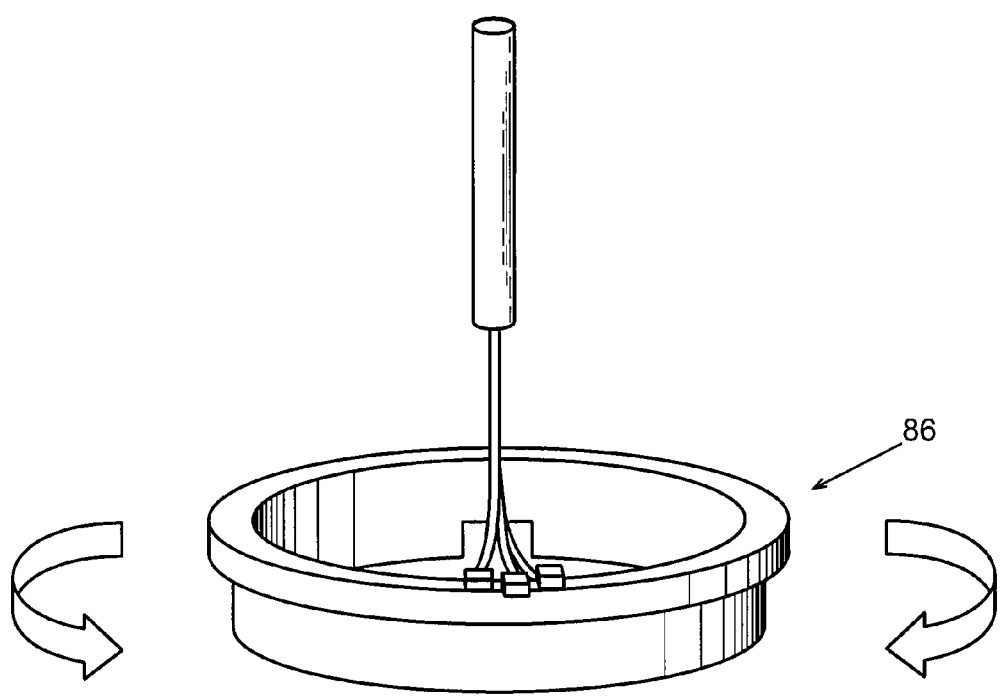
FIG. 8 is a schematicized perspective view of centrifuge usable to practice this invention.

Intermediate phase subsystem 14 may also include a centrifuge 86, as shown in FIG. 2 and in more detail in FIG. 8. Centrifuge 86 may be configured as a discontinuous flow-through channel in the shape of a ring that is spun about its axis. Functionally, the second mixture of the fluid and the first and second extraction solvents flow into the centrifuge ring through one port and exit centrifuge 86 as separated fluid and first and second extraction solvents. The second mixture may be sent to centrifuge 86 using gravity, a pump 88, such as a peristaltic pump or other type of pump, vacuum, or other means. The spinning action of centrifuge 86 generates centrifugal forces that separate the constituents of the second mixture. The mixture of the fluid having a small amount of first and second extraction solvent is sent to the final phase subsystem 16 through valve 90. The first and second extraction solvents that are separated from the fluid in centrifuge 86 are sent through valve 92 to either waste receptacle 40 or to a condenser 94. Condenser 94 is included in intermediate phase subsystem 14 if DEE is used as a first or second extraction solvent, and may be used with other solvents.

The initial phase subsystem 12 and intermediate phase subsystem 14 include various sensors 96 located throughout the system for monitoring pressure, temperatures, flow rates, solvent levels and other parameters. The sensors may be any conventional sensor for the parameter being measured.

3. Final Phase Subsystem

The final phase subsystem 16 removes at least a portion of the first extraction solvent and the second extraction solvent from the fluid that was not removed in the intermediate phase subsystem 14. The final phase subsystem 16 may be composed of at least two embodiments, as shown in FIGS. 9 and 10. Specifically, FIG. 9 shows a once-through system that is capable of removing at least a portion of the first and second extraction solvents from a fluid by passing the second mixture through the system only one time so that the concentrations of these solvents are less than a particular threshold, which may be about 10 ppm, thereby enabling the fluid to be administered to a patient without undesirable consequences. FIG. 10 depicts a recirculating subsystem that is also capable of reducing the concentration of the first and second extraction solvents to a level beneath a particular threshold. However, solvent concentrations are reduced to adequate levels by passing the second mixture through the subsystems one or more times. Each of these embodiments is discussed in more detail below.

(a) Once-Through Solvent Removal Subsystem

The once-through subsystem 99 depicted in FIG. 9 is composed of two HFCs 100 and 102 for removing the first and second extraction solvents from the fluid. However, the once-through subsystem may be composed of any number of HFCs depending on the effective surface area of the hollow fibers as calculated using the methodology and formulas previously described. The once-through subsystem includes a pervaporation buffer container 104 for receiving the fluid from intermediate phase subsystem 16. The pervaporation buffer container 104 is coupled to a container 106, which may be, but is not limited to, an air bag for containing the air that escapes from buffer container 104. The fluid may flow into HFC 100 by gravity, pump 108, which may be a peristaltic pump or other pump not having vanes that contact the fluid being pumped, or other means.

Pervaporation buffer container 104 is coupled to the lumens of hollow fibers 110 of HFC 100 so that a fluid may flow through the lumens of hollow fibers 110 during operation. The lumens of hollow fibers 110 of HFC 100 are in fluid communication with the lumens of hollow fibers 112 of HFC 102. A chamber 114, also referred to as the shell side of hollow fibers 112 of HFC 102 is capable of receiving a gas, such as air, nitrogen, or other material, such as mineral oil or the like. However, in another embodiment, the gas is sent through the lumens of hollow fibers 112 and the fluid is sent through HFC 102 on the shell side of hollow fibers 112. Chamber 114 of HFC 102 is coupled to a solvent removal system 116 and is in fluid communication with chamber 118 of HFC 100. Solvent removal system 116 cycles a material in a gaseous state through chambers 114 and 118 to remove the first and second extraction solvents from the fluid contained within lumens of hollow fibers 110 and 112. In certain embodiments, the gaseous material is common air, nitrogen, or other inert gas. Solvent removal system 116 may also cycle a mineral oil or other material through chambers 114 and 118.

Solvent removal system 116 includes a carbon bed 120, a first sterile filter 122, a pump 124, and a second sterile filter 126. These elements may be coupled together using a conduit, a coupling or other connection device. Carbon bed 120 is coupled to HFCs 100 and 102 for receiving gases having first and second extraction solvents. Carbon bed 120 removes most of the first and second extraction solvents from the gases being passed through the chambers 114 and 118 of HFCs 100 and 102. First sterile filter 122 and second sterile filter 126 are sterile barriers allowing the system to be partially disassembled without contaminating the entire system. Suitable filters may have a lipophilic or hydrophilic membranes. In another embodiment, the solvent removal system 116 may be composed of one or more filters, condensers or cold traps, or catalytic combustors to remove the solvent vapors from the gas before it is recycled through HFCs 100 and 102.

Final phase subsystem 16 also includes an output buffer container 128 for collecting the delipidated fluid after passing through the lumens of hollow fibers 110 and 112 of HFCs 100 and 102. Output buffer container 128 may be any container that is preferably sterile and capable of holding the delipidated fluid. A scale 130 may be included to determine the amount of fluid present in output buffer container 128 and for other analytical purposes.

Final phase subsystem 16 may also include at least one sensor 132 for sensing the presence of a solvent in the fluid leaving final phase subsystem 16. Various types of solvent sensors may be used as sensor 132. Preferably, the sensors are capable of detecting very low levels of solvent. One such sensor is capable of measuring differences in infrared absorption spectra between solvents and plasma. Using approaches known to those skilled in the art, several light sources and detectors can be integrated into a non-contact optical sensor that can be calibrated to measure the concentrations of one or all of the solvents. Another useful sensor includes a resistive sensor that uses a resistance processor to detect the presence of very low levels of solid particles, such as model number TGS2620 or TGS822 available from Figaro USA Inc., Glenview, Ill. Yet another type of optical sensor includes one that determines or identifies molecules comprising a solvent. Optionally, indirect measurement of solvent level in the fluid could be performed by measuring the amount of solvent in solvent removal system 116. However, direct measurement is more reliable, because an obstruction in filter(s) 122 or 126, or other flow impediment may falsely indicate that solvent has been extracted, when the solvent has in fact remained in the fluid.

HFCs 100 and 102 have been tested and successfully reduce total concentrations of solvents, such as di-isopropyl ether and di-ethyl ether, in water and plasmas, such as human and bovine plasma, using different HFCs, pressures, and flow rates, as shown in Table 1 below. Table 2 below shows the reduction in concentrations of DiPE in water, bovine plasma and human plasma as a function of time. HFCs 100 and 102 may have a total surface area of permeable membrane formed by the hollow fibers between about 4,200 square centimeters and about 18,000 square centimeters, depending on the type of HFC used. Further, the gas flow rate was varied between about 2 liters per minute to about 10 liters per minute, and the plasma flow rate was varied between about 10 mL per minute to about 60 mL per minute. Operating the once-through final subsystem 99 in this manner can reduce the initial concentrations of solvents from between about 28,000 ppm and 9,000 ppm to between about 1327 ppm and about 0.99 ppm within between about 14 minutes and 30 minutes.

TABLE 1

| Module (Quantity) | Orientation | Phase | Lumen Flow rate (cc/min) | Air Flow (L/min) | Pressure before HFC (psig) | Pressure after HFC (psig) | Carbon (g) | Volume Treated (L) | Initial DIPE conc ppm | Final DIPE conc ppm |
|---|---|---|---|---|---|---|---|---|---|---|
| Effect of Module | | | | | | | | | | |
| Fresenius F6 (1) & F8 (1) | Horiz | $H_2O$ | 20 | 9.3 | 0.44 | −0.74 | 100 | 0.75 | 9045 | 1327 |
| Spectrum 11200 $cm^2$ (2) | Horiz | $H_2O$ | 20 | ~9 | −0.13 | −1.01 | 100 | 0.75 | 9684 | 3 |
| Celgard (1) | Vertical | $H_2O$ | 20 | 11 | −0.2 | −1.21 | 100 | 0.5 | 10518 | 0.99 |
| Spectrum 11200 $cm^2$ (2) | Horiz | Human Plasma | 20 | 9.2 | 0.91 | −0.06 | 100 | 0.75 | 12200 | 6 |

TABLE 1-continued

| Module (Quantity) | Orientation | Phase | Lumen Flow rate (cc/min) | Air Flow (L/min) | Pressure before HFC (psig) | Pressure after HFC (psig) | Carbon (g) | Volume Treated (L) | Initial DIPE conc ppm | Final DIPE conc ppm |
|---|---|---|---|---|---|---|---|---|---|---|
| Celgard (2) | Vertical | Human | 20 | 10.1 | −0.16 | −1.3 | 150 | 0.25 | 27822 | 9 |
| Spectrum 11200 cm² (2) | Horiz | H₂O | 18 | | 0.71 | −0.83 | | 0.75 | 9055 | 18 |
| Spectrum 11200 cm² (2) | Horiz | H₂O | 20 | | 0.65 | −0.88 | | 0.75 | 8851 | 22 |
| Spectrum 11200 cm² (2) | Horiz | H₂O | 40 | | 0.7 | −0.85 | | 0.75 | 10016 | 11 |
| Spectrum 11200 cm² (2) | Horiz | H₂O | 60 | | 0.65 | −0.82 | 100 | 0.75 | 10134 | 93 |
| Celgard (1) | Vertical | H₂O | 20 | 9.3 | 0.44 | −0.2 | 100 | 0.75 | 7362 | 22 |
| Celgard (1) Effects of Pressure | Vertical | H₂O | 40 | 9.2 | 0.44 | −0.2 | 100 | 0.75 | 9366 | 193 |
| Celgard (2) | Vertical | Human | 20 | 9.7 | 0.11 | −1.33 | 100 | 0.25 | 18782 | ND |
| Celgard (2) | Vertical | Human | 20 | 9.2 | −1.39 | −2.93 | 100 | 0.25 | 15246 | ND |
| Celgard (2) Full Body Volume | Vertical | Human | 20 | 8.1 | −2.79 | −4.12 | 100 | 0.25 | 13144 | ND |
| Celgard (2) | Vertical | Human | 20 | 5.3 | −1.1 | −1.8 | 300 | 3100 | 9040 | 24 |

TABLE 2

| | DIPE concentrations [ppm] | | |
|---|---|---|---|
| Time [min] | Water | Bovine | Human (Norm) |
| 0 | 6782.094027 | 9473.974574 | 11351.10738 |
| 2 | 1716.182938 | 3012.065643 | 3868.491245 |
| 4 | 118.591244 | 485.1426701 | 636.1926821 |
| 6 | 16.36572648 | 102.9572692 | 125.8618995 |
| 8 | 5.364620368 | 36.33996072 | 60.440048 |
| 10 | 4.230662874 | 16.08489373 | 34.50180421 |
| 12 | 2.019251402 | 23.54890574 | 16.71332069 |
| 14 | 1.537721419 | 9.218693213 | 17.32898791 |
| 16 | 3.169227108 | 6.549024255 | 15.26858655 |

Various control devices are included in final phase subsystem 16. For instance, the once-through subsystem includes a fluid level sensor 134 and a temperature sensor 136 coupled to pervaporation buffer container 104, a fluid level sensor 138, a fluid presence detector 140, an encoder 142 and a current overload detector 144 for controlling pump 108, and a pressure sensor 146. Solvent removal system 116 includes a fluid presence detector 148, a temperature sensor 150, a current overload detector 152 for controlling pump 124, and pressure sensors 154 and 156.

(b) Recirculating Solvent Removal Subsystem

The recirculating solvent removal subsystem 218 is configured much like the once-through subsystem. FIG. 10 depicts the recirculating system as including two HFCs 160 and 162 for removing the first and second extraction solvents from the fluid. While the embodiment depicted in FIG. 10 includes two HFCs positioned in parallel, the subsystem may be composed of any number of HFCs positioned in parallel, series, or other configuration. In another embodiment, the subsystem may be composed of only a single HFC.

HFCs 160 and 162 are preferably sized according to the calculations and methodology set forth above. HFCs 160 and 162 contain hollow fibers 164 and 166, respectively, for receiving the fluid mixed with residual first and second extraction solvents, referred to as the second mixture, from intermediate phase subsystem 14. The biological flows from intermediate phase subsystem 14 to a recirculation vessel 168. Recirculation vessel 168 receives the fluid mixture from the intermediate phase subsystem 14 and from HFCs 160 and 162. The mixture of fluid and remaining first and second extraction solvents not removed in intermediate phase subsystem 14 is sent to HFCs 160 and 162 using gravity flow, a pump 170, which may be a peristaltic pump or other pump not having vanes that contact the fluid being pumped, vacuum, or other means. The second mixture flows through the lumens of hollow fibers 164 and 166 of HFCs 160 and 162 while a gaseous material, such as common air or nitrogen or other inert gas, or other material is passed through chambers 172 and 174 of HFCs 160 and 162, respectively, or vice versa. Chambers 172 and 174 are also referred to as the shell sides of HFCs 160 and 162. The second mixture is circulated between recirculation vessel 168 and HFCs 160 and 162 until a sensor 176 detects that the concentration of the first and second extraction solvents in the fluid is less than a predetermined threshold, such as less than about 10 ppm or below about 50 milligrams of solvent per 3.5 liters of fluid, for allowing the fluid to be administered to a patient without undesirable consequences. The fluid is then sent to output buffer 210 by closing valve 212 and opening valve 214. The amount of fluid present in output buffer 210 may be determined using scale 216.

The recirculating subsystem 218 also includes a number of control devices. For instance, the recirculating subsystem 218 includes fluid level sensors 196 and 198, a fluid presence detector 200, a current overload detector 202 and an encoder 204 for controlling pump 170, a pressure sensor 206, and a temperature sensor 208. These sensing devices are used for controlling the system 218.

A solvent removal system 178 is included within the recirculating subsystem 218 for removing the first and second extraction solvents from the gas. Solvent removal subsystem 178 routes the gas through recirculation vessel 168 to allow more solvent from the fluid contained in vessel 168 to be removed. Solvent removal subsystem 178 includes a carbon bed 180 for removing solvents from the air, a first sterile filter 182 and a second sterile filter 184 for allowing the solvent removal system 178 to be partially disassembled without contaminating the entire system. Suitable filters may have a lipophilic or hydrophilic membranes. In an alternative embodiment, solvent removal subsystem 178 may be composed of one or more filters, condensers or cold traps, or catalytic combustors to remove the solvent vapors from the gas before it is recycled through HFCs 160 and 162. A pump 186 may be provided for circulating the gas through the subsystem. Solvent removal subsystem 178 may also include a temperature sensor 188, pressure sensors 190 and 192, and a current overload sensor 194 for controlling pump 186.

HFCs 160 and 162 have been tested and successfully reduce total concentrations of solvents, such as di-isopropyl ether and di-ethyl ether, in water and plasmas, such as human and bovine plasma, as shown in Table 3 below. HFCs 160 and 162 may have a total surface area of permeable membrane formed by the hollow fibers between about 4,200 square centimeters and about 18,000 square centimeters, depending on the type of HFC used. Further, the gas flow rate was varied between about 2 liters per minute to about 14 liters per minute, and the plasma flow rate was varied between about 9 mL per minute to about 900 mL per minute. Operating the recirculating subsystem 218 in this manner can reduce the initial concentrations of solvents, such as DiPE and DEE, from between about 31,000 ppm and 9,400 ppm to between about 312 ppm and about 2 ppm within between about 14 minutes and 80 minutes.

of 80 mL. Further, centrifuge 81 had a relative centrifugal force (RCF) of 560 times gravity (506×g).

The second mixture was then introduced into a final phase subsystem 218 as shown in FIG. 10. The second mixture was circulated through HFCs 160 and 162 at a flow rate of about 750 mL/min, wherein each HFC had a holdup volume of about 50 mL and an area of about 4200 $cm^2$. Air was circulated through the shell side of hollow fibers 164 and 166 of HFCs 160 and 162 to extract the residual first and second extraction solvents from the fluid. Carbon bed 180 was used to remove solvent vapors in the recirculating gas stream. This process was continued until the solvent vapor detector 176 indicated that solvent levels were below a particular threshold, such as below 10 ppm or below about 50 milligrams of solvent per 3.5 liters of fluid, enabling the remaining solvent to be removed with a final pass through the carbon bed 180. Upon indication that sufficient levels of solvent were removed, the fluid was then tested to determine the effectiveness of the apparatus.

The process resulted in a reduction of cholesterol of about 90 percent, which was measured by standard lipid profile enzymatic assays that are known in the art. For a volume of approximately 300 mL of plasma and using discontinuous subsystems emulating the system described above, the

TABLE 3

| Lumen Material | Solvent to be Removed | Shell Material | Shell Flow | Lumen Flow | Module (Surface Area) | Initial Solvent Conc (ppm) | Final Solvent Conc (ppm) | Time recirculating |
|---|---|---|---|---|---|---|---|---|
| Water | Diethyl Ether | Air | 7 L/min | 220 | Fresenius F80A (18000 cm2) | 31000 | 265 | 30 min |
| Water | Diisopropyl Ether | Air | 12.3 L/min | 750 | Celgard (8400 cm2) | 6782 | 2 | 14 min |
| Bovine Plasma | Diisopropyl Ether | Air | 12.3 L/min | 750 | Celgard (8400 cm2) | 9473 | 7 | 16 min |
| Human Plasma | Diisopropyl Ether | Air | 12.3 L/min | 750 | Celgard (8400 cm2) | 11351 | 15 | 16 min |
| Water | Diisopropyl Ether | Heavy Mineral Oil | 10 cc/min | 4 cc/min | Spectrum (8000 cm2) | 4635 | 312 | 80 min |

4. Example of Use

As described above, the delipidation device depicted schematically in FIG. 2 is capable of removing at least a portion of a total concentration of lipids or lipid-containing organisms from a fluid. In this particular example, the fluid used was a bovine plasma. The bovine plasma was first introduced into the lumens of hollow fibers 20 of HFC 18 at a flow rate of 50 mL/min and contacted with a first extraction solvent located in chamber 22 of HFC 18, which is the shell side of hollow fibers 20. The first extraction solvent was composed of a mixture of about 60 percent di-isopropyl ether (DiPE) and about 40 percent n-butanol and was sent through HFC 18 at a flow rate of 200 mL/min. As described above, this produced a first mixture of plasma and first extraction solvent in the lumens of hollow fibers 20. The first mixture was then washed with a second extraction solvent, which was composed of diethyl ether (DEE), in DTCs 44 and 46, which were about 20 inches long and about 0.375 inches in diameter and positioned in series. Sending the first mixture through DTCs 44 and 46 reduced the concentration of lipids in the fluid or lipid-containing organisms, or both, and formed a second mixture composed of plasma and the first and second extraction solvents. The resulting plasma from the final DTC wash was circulated through vortexer 72 and centrifuge 81 for about 6 sequential washes. Vortexer 72 had a capacity of 500 mL, and centrifuge 81 had a capacity delipidation process described above takes approximately 20 minutes, thereby achieving a delipidation throughput of about 15 mL/min.

B. Second Embodiment

1. Initial Phase Subsystem

Figure 11:
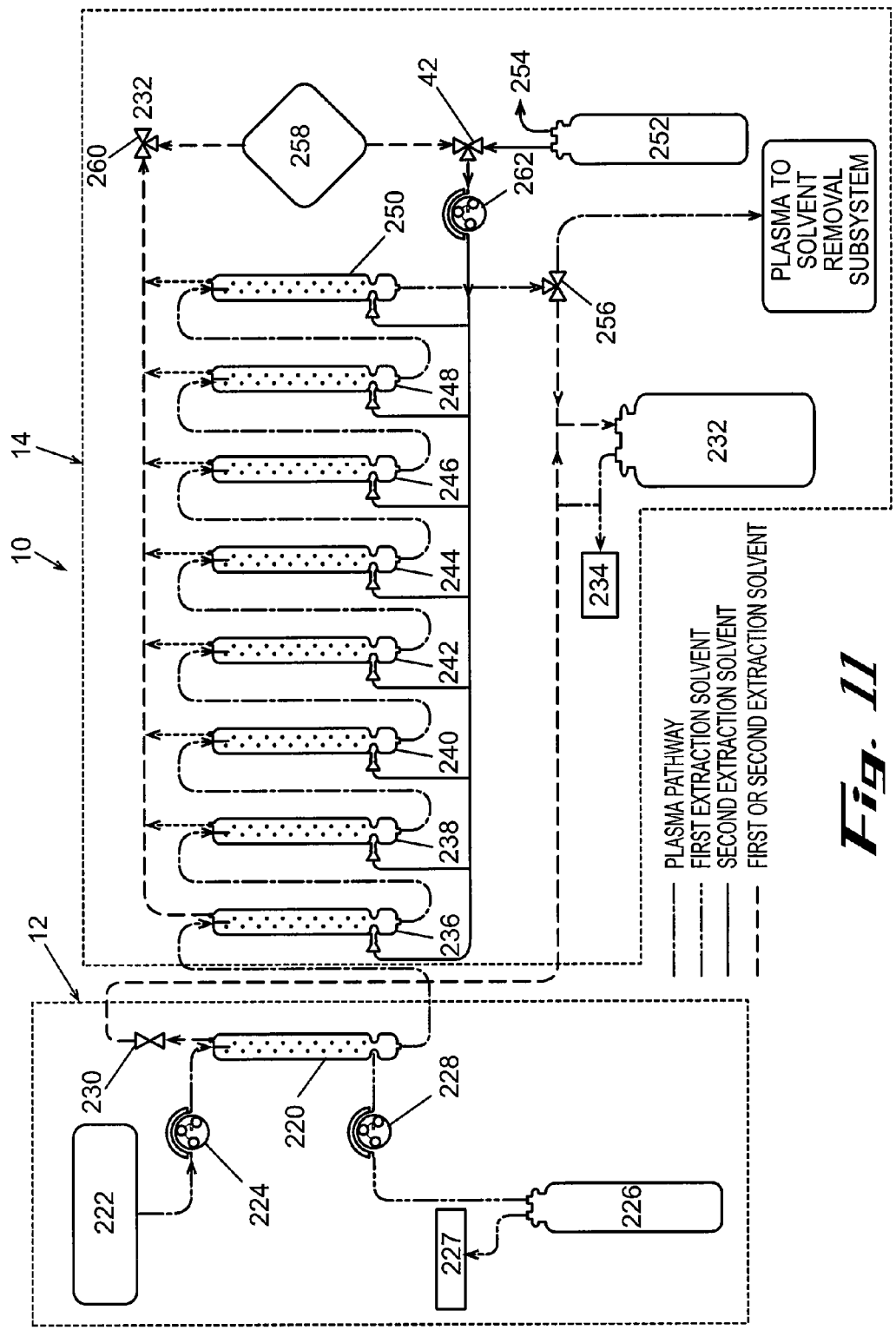
FIG. 11 is a schematic diagram of a second embodiment of this invention showing the initial phase subsystem and the intermediate phase subsystem.

FIG. 11 depicts an initial phase subsystem 12 composed of a DTC 220 for contacting a first extraction solvent with a fluid containing lipids or lipid-containing organisms, or both, and for removing at least a portion of the total concentration of lipids from the fluid. While FIG. 11 shows a single DTC, initial phase subsystem 12 may be composed of one or more DTCs coupled in series or parallel or any combination thereof. DTC 220 may be configured as shown in FIG. 5.

DTC 220 is in fluid communication with a fluid source 222 for receiving a fluid. Fluid source 222 may be positioned to feed the fluid to DTC 220 using gravity flow, a vacuum, a pump 224, which may be a peristaltic pump or other pump not having vanes that contact the fluid being pumped, or other means. DTC 220 contains a first extraction solvent supplied by first extraction solvent source 226 via gravity, a vacuum, pump 228, which may be a peristaltic pump, centrifugal pump or other suitable pump, or other suitable means. First extraction solvent source 226 includes a vent 227 for safe operation. As described above, DTC 220 contains a dispersion device, which is typically a small gauge needle for inserting the fluid into DTC 220 as a fine dispersion. At least a portion of the lipids contained within the fluids separate and dissolve in the first extraction solvent. This mixture of solvent and dissolved lipids in DTC 220 are transferred through valve 230 to waste receptacle 232, which includes a vent 234 for safe operation. The fluid that is placed into DTC 220 falls through the first extraction solvent and comes to rest in the bottom portion of DTC 220. The fluid is then taken from DTC 220 and sent to intermediate phase subsystem 14 as a first mixture of fluid and first extraction solvent.

2. Intermediate Phase Subsystem

Intermediate phase subsystem 14 shown in FIG. 11 includes eight DTCs 236–250 for removing at least a portion of the lipids contained within the fluid that were not removed within initial phase subsystem 12. While FIG. 11 shows eight DTCs, intermediate phase subsystem 14 may be composed on any number of appropriately sized DTCs, such as one or more. Further, the DTCs may be configured in series, as shown in FIG. 1, or in parallel, or in any combination thereof. DTC 236 receives a first mixture of the fluid and the first extraction solvent from DTC 220 of initial phase subsystem 12. Each DTC 236–250 is filled with a second extraction solvent received from second extraction solvent source 252. Second extraction solvent source 252 also includes a vent 254 for safe operation.

The first mixture of fluid containing lipids or lipid-containing organisms, or both, and first extraction solvent is sent through each of DTCs 236–250. During operation of intermediate phase subsystem 14, at least a portion of the first extraction solvent that mixed with the fluid in initial phase subsystem 12. Further, the second extraction solvent may remove a portion of the lipids that may not have been separated from the fluid by initial phase subsystem 12. Also, a portion of the second extraction solvent may mix with the mixture of fluid and first extraction solvent to form a second mixture. This second mixture of fluid and first and second extraction solvents is then sent to final subsystem 16 through valve 256. The waste second extraction solvent may include lipids and first extraction solvent removed from the fluid. The waste extraction solvent is removed from DTCs 236–250 using gravity, a vacuum, pump 262, or other means and may either be sent through condenser 258 or to waste receptacle 232 using valve 260. Pump 262 may be either a peristaltic pump or other type pump.

3. Final Phase Subsystem

The embodiment of the delipidation system 10 shown in FIG. 11 may be used with either the once-through subsystem 99 shown in FIG. 9 or the recirculating subsystem 218 shown in FIG. 10. However, this embodiment of delipidation system 10 is not limited to being used with these embodiments of final phase subsystem 16. Rather, this embodiment of delipidation system 10 shown in FIG. 11 may be used with any system capable of reducing the concentrations of first and second extraction solvents in the fluid to a level beneath a particular threshold enabling the fluid to be administered to a patient without undesirable consequences. The threshold may be, but is not limited to, about 10 ppm or below about 50 milligrams of solvent per 3.5 liters of fluid.

4. Example of Use

As described above, the delipidation device depicted schematically in FIG. 11 is capable of removing at least a portion of a total concentration of lipids from a fluid or from lipid-containing organisms, or both. In this particular example, the fluid used was bovine plasma. The bovine plasma was sent to DTC 220 at a flow rate of 15 mL/min where it contacted a first extraction solvent, which was composed of about 60 percent DiPE and about 40 percent n-butanol. The first extraction solvent was added to DTC 220 before the introduction of plasma at a flow rate of about 200 mL/min. Contacting the first extraction solvent with the plasma caused lipids to separate from the plasma and to form a first mixture of plasma and first extraction solvent. Similarly, lipids in lipid-containing organisms may be removed by the first extraction solvent.

The first mixture was then washed with a second extraction solvent, which was diethyl ether (DEE), in a series of DTCs 236–250, which were about 20 inches long and about 0.375 inches in diameter. The process created a second mixture composed of the plasma and first and second extraction solvents. At least a portion of the lipids contained in the plasma was removed after passing the first mixture only one time through the DTCs forming intermediate phase subsystem 14, which was observed as the initially turbid plasma becoming clearer with a single pass through the DTCs containing DEE. In addition, at least a portion of the n-butanol was removed. The flow rate through the intermediate phase subsystem 14 was approximately 15 mL/min.

The second mixture was then introduced into a final phase subsystem 218 as shown in FIG. 10. The second mixture was circulated through HFCs 160 and 162 at a flow rate of about 750 mL/min, wherein each HFC had a holdup volume of about 50 mL and an area of about 4200 $cm^2$. Air was circulated through the shells of HFCs 160 and 162 to extract the residual first extraction solvent from the fluid. This process was continued until the solvent vapor detector 176 indicated that solvent levels were below a particular threshold enabling the remaining solvent to be removed with a final pass through the carbon bed 180. Upon indication that sufficient levels of solvent were removed enabling the fluid to be returned to a patient without undesirable effects, the fluid was then tested to determine the effectiveness of this embodiment.

The process resulted in a reduction of cholesterol of about 90 percent, which was measured by standard lipid profile enzymatic assays that are known in the art. For a volume of approximately 300 mL of plasma and using discontinuous subsystems emulating the system described above, the delipidation process takes approximately 20 minutes, thereby achieving a delipidation throughput of about 15 mL/min.

C. Third Embodiment

1. General Description

Figure 12:
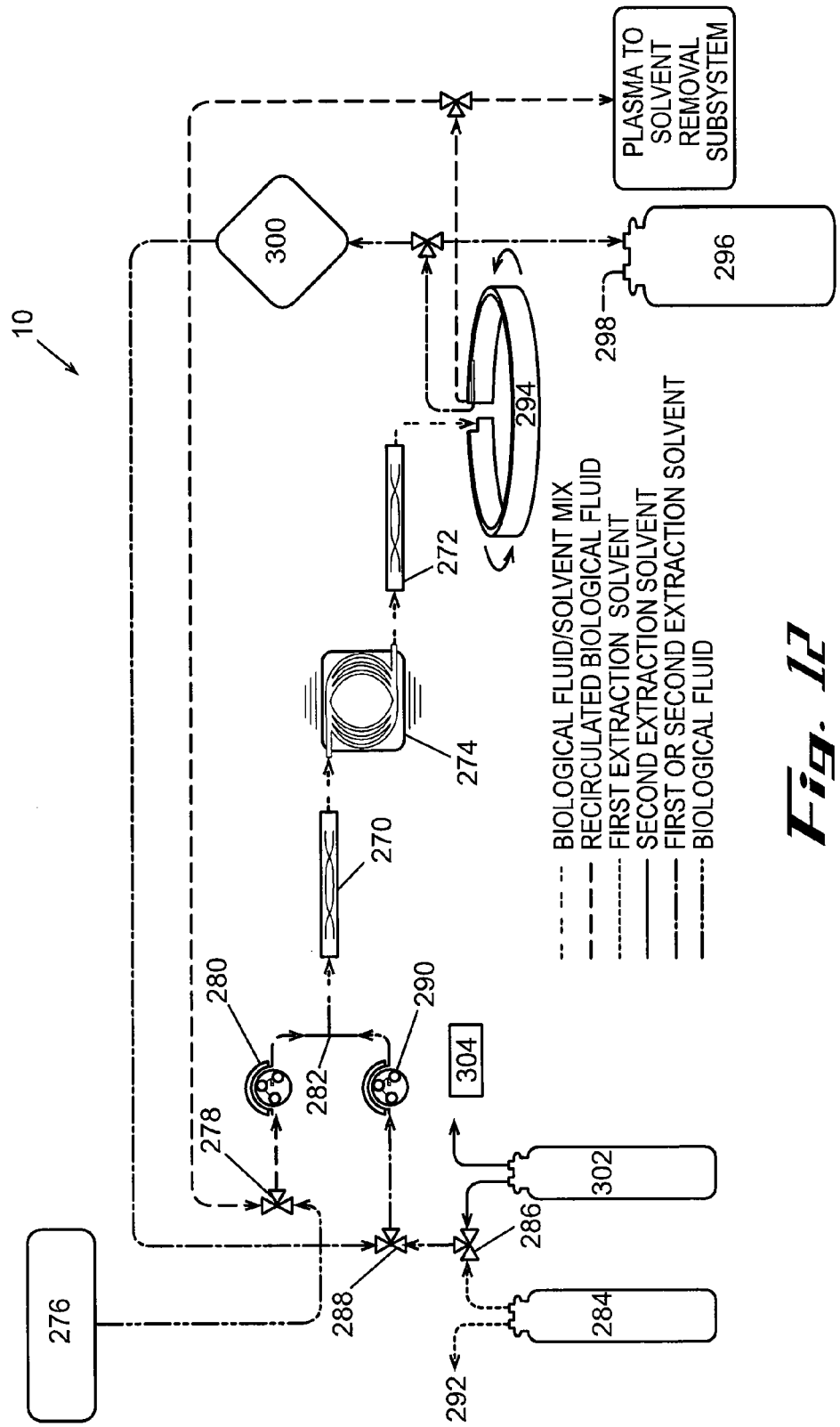
FIG. 12 is a schematic diagram of a third embodiment of this invention showing a single apparatus for performing the initial phase and the intermediate phase of the delipidation method.

FIG. 12 depicts a portion of another embodiment of delipidation system 10 which includes initial phase subsystem and intermediate phase subsystem. This embodiment may be used together with the final phase subsystems shown in FIGS. 9 and 10 as described in more detail below. Unlike the previous systems described above, this embodiment does not use different apparatuses to complete the initial and intermediate phases of the delipidation process. Rather, this embodiment uses a single apparatus for completing the initial and intermediate phases of the delipidation process.

Specifically, FIG. 12 depicts in-line static mixers 270 and 272 coupled to both inlet and outlet sides of a vortexer 274. In-line static mixers 270 and 272 may be formed from many designs, but typically include single or multiple tubes containing one or more flow vanes along their length. Further, this embodiment is not limited to two in-line static mixers, but may comprise any number of in-line mixers coupled in series or parallel configuration, or any combination of these configurations. The vanes cause mixing and shearing of the fluids passed through the mixers. The amount of mixing and shearing can be regulated by changing the flow rates of the fluid through mixers 270 and 272. An example of in-line static mixers 270 and 272 are available from Cole-Parmer Instrument Company, Vernon Hills, Ill. as Catalog Part Number U-04668-14.

Vortexer 274 may be a continuous vortexer, as shown in FIG. 6, or a batch vortexer, as shown in FIG. 7. Furthermore, the configuration of this embodiment is not limited to the design shown in FIG. 12. For instance, vortexer 274 may be positioned before in-line static mixer 270 or after in-line static mixer 272. As previously described, these vortexers operate upon receiving external vibration that causes vortices to form in each tube. The non-rotating vortexer 274 is advantageous because of its simplistic design that is less expensive than more complicated designs. Thus, it may be used more efficiently than other devices in a disposable system. Further, vortexer 274 does not contain any bushings, bearings or moving parts that are subject to failure.

In-line static mixer 270 receives a fluid from a fluid source 276 through valve 278 via gravity, a vacuum, a pump 280, or other means. Prior to the fluid entering in-line static mixer 270, the fluid mixes with a first extraction solvent at T-connection 282. The first extraction solvent is supplied from a first extraction solvent source 284 through valves 286 and 288 via gravity, pump 290, which may be a peristaltic pump, centrifugal pump, or other type pump, or other means. First extraction solvent source 284 includes vent 292 for safe operation.

A centrifuge 294 may be positioned in-line down stream of in-line static mixers 270 and 272 and vortexer 274. Centrifuge 294, as shown in FIG. 8, is configured as a discontinuous flow-through channel in the shape of a ring that is spun about its axis. However, centrifuge 294 is not limited to this configuration. Rather, centrifuge 294 may be any centrifuge. Centrifuge 294 separates the fluid from the first and second extraction solvents.

During operation, a fluid is sent from fluid source 276 to in-line static mixer 270. A first extraction solvent mixes with the fluid at T-connection 282 prior to the fluid entering in-line static mixer 276. The fluid and first extraction solvent pass through in-line static mixers 270 and 272 and vortexer 274 where at least a portion of the lipids contained within the fluid or in lipid-containing organisms are separated and dissolve into the first extraction solvent. The first mixture of first extraction solvent and fluid passes through centrifuge 294 where the first extraction solvent is separated from the fluid. The fluid is sent back to valve 278, and the first extraction solvent separated from the fluid is deposited in waste receptacle 296, which may include vent 298, or circulated through condenser 300 to valve 288 to be mixed with a fluid. The fluid may be sent through in-line static mixers 270 and 272 one or more times during the initial phase.

The intermediate phase of the delipidation system 10 is conducted using in-line static mixers 270 and 272 and vortexer 274. Specifically, the first mixture composed of the fluid and residual first extraction solvent not completely removed by centrifuge 294 is sent through T-connection 282 and mixes with a second extraction solvent to form a second mixture. The second mixture solvent is contained in a second extraction solvent source 302, which may include a vent 304 for safe operation. The second mixture of and first and second extraction solvents is sent through in-line static mixers 270 and 272 and vortexer 274 where a portion of the first extraction solvent may be removed. For example, in one embodiment in which the first extraction solvent is a mixture of DiPE and n-butanol, the second extraction solvent separates at least a portion of the n-butanol from the mixture of first extraction solvent and the fluid. The second extraction solvent may also separate a portion of the lipids from the fluid not removed while using the first extraction solvent. The separated lipids may dissolve in the first or second extraction solvents, or both. The second mixture is sent through centrifuge 294 where the fluid and the first and second extraction solvents are separated. After passing through centrifuge 294, the fluid contains small amounts of first and second extraction solvents and is sent to final phase subsystem 16 for removal of these remaining amounts of the first and second extraction solvents. The first and second extraction solvents are then sent to waste receptacle 296.

This embodiment may be used in cooperation with a subsystem capable of removing at least a portion of the first and second extraction solvents from the fluid after it has passed through initial and intermediate phase subsystems. For example, this embodiment may be combined with the once-through subsystem 99 shown in FIG. 9 or the recirculating subsystem 218 shown in FIG. 10. Each of these subsystems is explained in more detail in Sections III.A.3(a) and (b) above.

2. Example of Use

As described above, the delipidation device depicted schematically in FIG. 12 is capable of removing at least a portion of a total concentration of lipids from a fluid containing lipids or from lipid-containing organisms, or both. In this particular example, bovine plasma was used as the fluid. The bovine plasma was introduced to in-line static mixer 270, as shown for instance in FIG. 12, at a flow rate of about 50 mL/min where it contacted a first extraction solvent, which was composed of about 60 percent DiPE and about 40 percent n-butanol. The first extraction solvent was added to in-line static mixer 270 at a flow rate of about 50 mL/min. Contacting the first extraction solvent with the plasma caused lipids to separate from the fluid and form a first mixture of plasma and first extraction solvent. The first mixture was then circulated through vortexer 274. The vortexer 274 had a capacity of 500 mL, and the centrifuge 294 had a capacity of 80 mL. The first mixture was then sent through in-line static mixer 272. The first mixture then circulated through centrifuge 294, which had a relative centrifugal force (RCF) equal to about 560 times gravity (560×g). Multiple passes through the circulation loop may be required to achieve the desired delipidation result. Further, a second extraction solvent may also be used, preferably a diethyl ether (DEE) solvent, to achieve the desired amount of removal of a first extraction solvent. Adding a second extraction solvent to the first mixture forms a second mixture composed of the plasma and the first and second extraction solvents.

The second mixture was then introduced into a final phase subsystem as shown in FIG. 10. The second mixture was circulated through HFCs 160 and 162 at a flow rate of about 750 mL/min, wherein each HFC had a holdup volume of about 50 mL and an area of about 4200 cm$^2$. Air was circulated through the shells 172 and 174 of HFCs 160 and 162 to extract the residual first extraction solvent from the fluid. This process was continued until the solvent vapor detector 176 indicated that solvent levels were below a particular threshold enabling the remaining solvent to be removed with a final pass through the carbon bed 180. Upon indication that sufficient levels of solvent were removed, the fluid was then tested to determine the effectiveness of the apparatus.

The total percentage of lipid extracted as measured by reduction of total cholesterol was about 80 percent, as measured by standard lipid profile enzymatic assays that are known in the art. This method can produce fluid having a reduced concentration of lipids or lipid-containing organisms at a rate of about 50 mL/min. This apparatus successfully removed about 85 percent of the total concentration of cholesterol, about 64 percent of triglycerides, about 64 percent phospholipids and about 96 percent high density lipoproteins (HDL) using discontinuous subsystems emulating the system described above.

D. Fourth Embodiment

1. General Description

Figure 13:
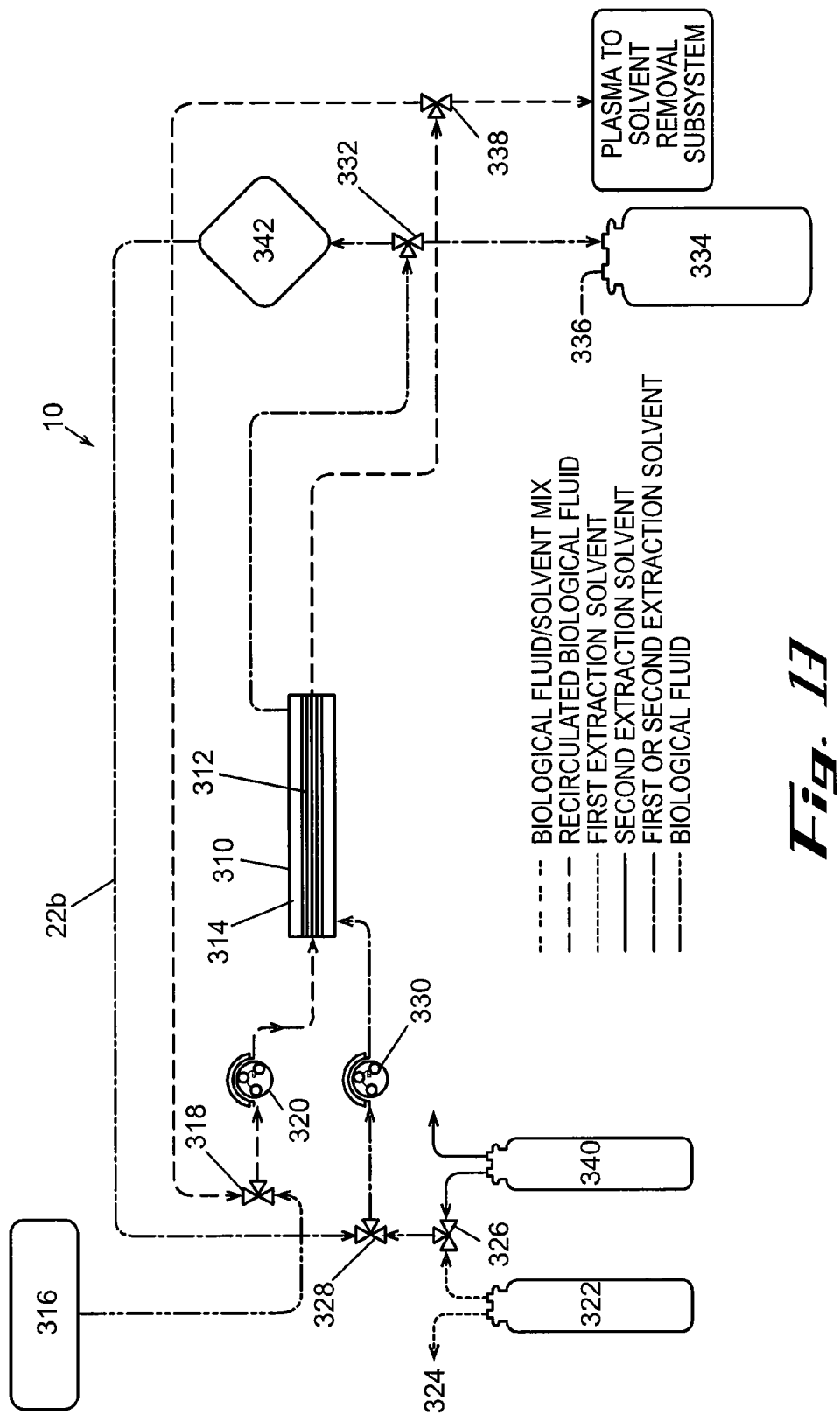
FIG. 13 is a schematic diagram of a fourth embodiment of this invention showing a single apparatus for performing the initial phase and the intermediate phase of the delipidation method.

FIG. 13 depicts a delipidation system 10 that is similar to the embodiment shown in FIG. 12. However, in-line static mixers 270 and 272 and vortexer 274 have been replaced with HFC 310. While FIG. 13 shows a single HFC, the embodiment may include one or more HFCs configured in parallel or in series, or in any combination thereof. HFC 310 may be constructed as described above, including hollow fibers 312 and a chamber 314, that is also referred to as the shell side of hollow fibers 312. As in the embodiment shown in FIG. 12, one apparatus is capable of performing the initial and intermediate phases of delipidation.

HFC 310 receives a fluid containing lipids or lipid-containing organisms, or both, from a fluid source 316, which may be a container, patient or other fluid source, through valve 318 via gravity, pump 320, or other means. Pump 320 may be a peristaltic pump or other pump not having vanes that contact the fluid being pumped. The fluid is sent through the lumens of hollow fibers 312 of HFC 310 to contact the fluid with a first extraction solvent. The first extraction solvent is contained within a first extraction solvent source 322 which may have vent 324 for safe operation. The first extraction solvent is sent from first extraction solvent source 322 through valves 326 and 328 via gravity, pump 330, which may be a peristaltic pump, centrifugal pump or other type pump, or other means.

The first extraction solvent crosses the pores of HFC 310 and causes at least a portion of the lipids contained within the fluid to separate. At least a portion of the separated lipids diffuse through the pores of hollow fibers 312 and return to chamber 314. However, some of the first extraction solvent that diffused the pores into the lumens of hollow fibers 312 will remain in the fluid to form a first mixture composed of the first extraction solvent and the fluid. Further, a portion of the lipids that separate from the fluid may attach to the inside surface of the lumens of hollow fibers 312. The first extraction solvent located in chamber 314 flows through HFC 310 and valve 332 and into waste receptacle 334, which may have a vent 336 for safe operation, or through condenser 342 to be used in HFC 310 once again. The first mixture of fluid and first extraction fluid flows from the lumens into hollow fibers 312 through valve 338 and is returned to the upstream side of HFC 310.

The intermediate phase of the delipidation process may be conducted by sending the mixture of fluid and the first extraction solvent through the lumens of hollow fibers 312 of HFC 310 to contact a second extraction solvent located in chamber 314. In one embodiment, HFC 310 is the same HFC used in the initial phase. In an alternative embodiment, HFC 310 may be replaced or reoriented so that the flow through the lumens of hollow fibers 312 or chamber 314, or both, is reversed. The second extraction solvent is sent from a second extraction solvent source 340 to chamber 314 of HFC 310 through valves 326 and 328 via gravity, a vacuum, pump 330, or other means. At least a portion of the second extraction solvent crosses the pores of hollow fibers 312 and mixes with the mixture of fluid and first extraction solvent removing at least a portion of a first extraction solvent. For example, in one embodiment in which a first extraction solvent is a mixture of n-butanol and DiPE, a second extraction solvent removes at least a portion of the n-butanol from the mixture. The second extraction solvent may also cause lipids to separate from the fluid. A portion of the separated lipids may attach to the inside surface of hollow fibers 312 and a portion of the separated lipids may dissolve in the second extraction solvent and cross the pores of hollow fibers 312 into chamber 314.

At the conclusion of the intermediate phase of the delipidation process, the fluid contains a small amount of first and second extraction solvents and is referred to as a second mixture. This mixture is sent through valve 338 to a system capable of extracting at least a portion of the second extraction solvent from the fluid to reduce the concentration of this solvent to a level enabling the fluid to be administered to a patient without potentially adverse consequences. Examples of systems capable of removing the second extraction solvents are the once-through subsystem 99, shown in FIG. 9, and the recirculating subsystem 218, shown in FIG. 10, as fully described above. However, this invention is not limited to these embodiments.

Figure 18:
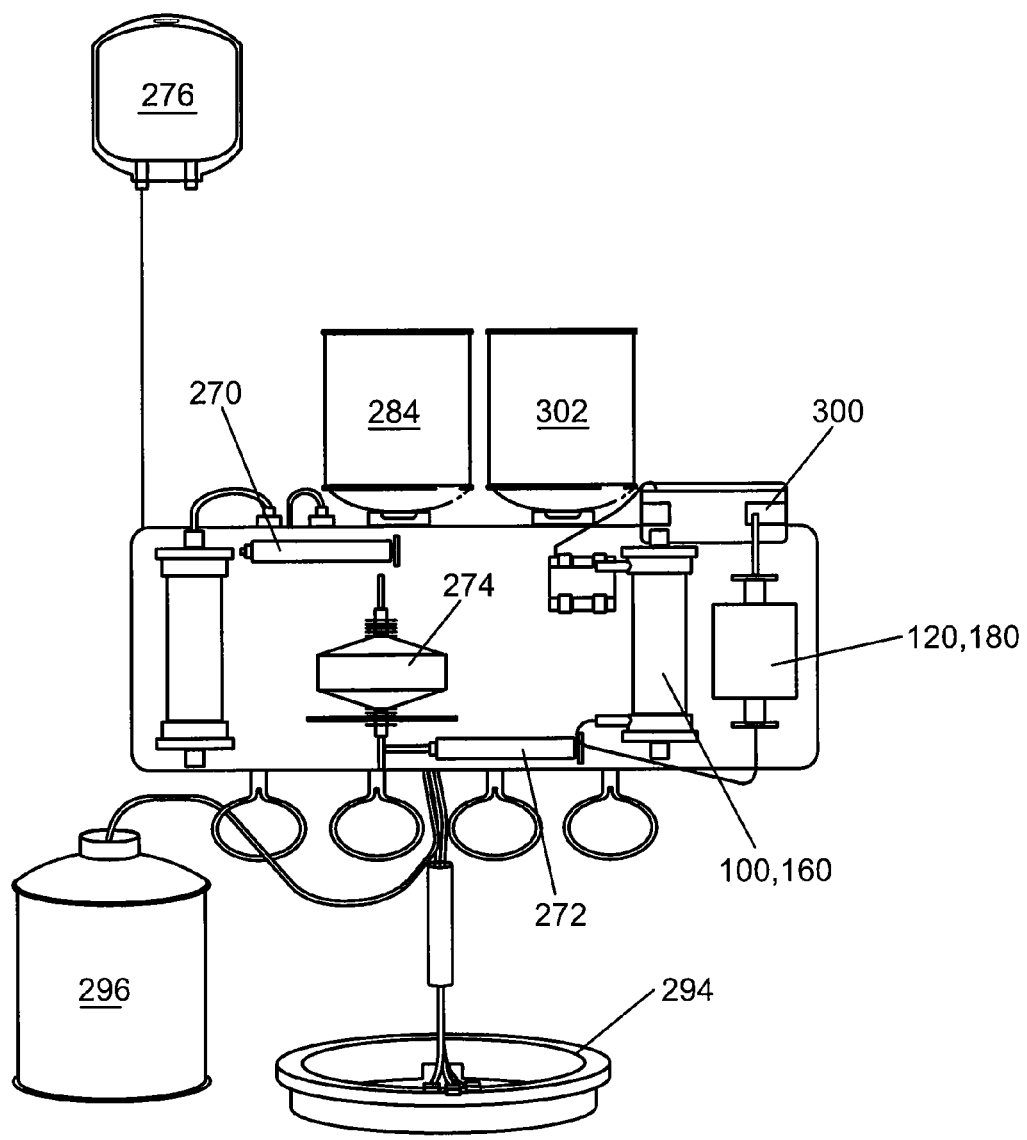
FIG. 18 is a schematicized perspective view of the device of FIG. 12 contained in a module.
Figure 19:
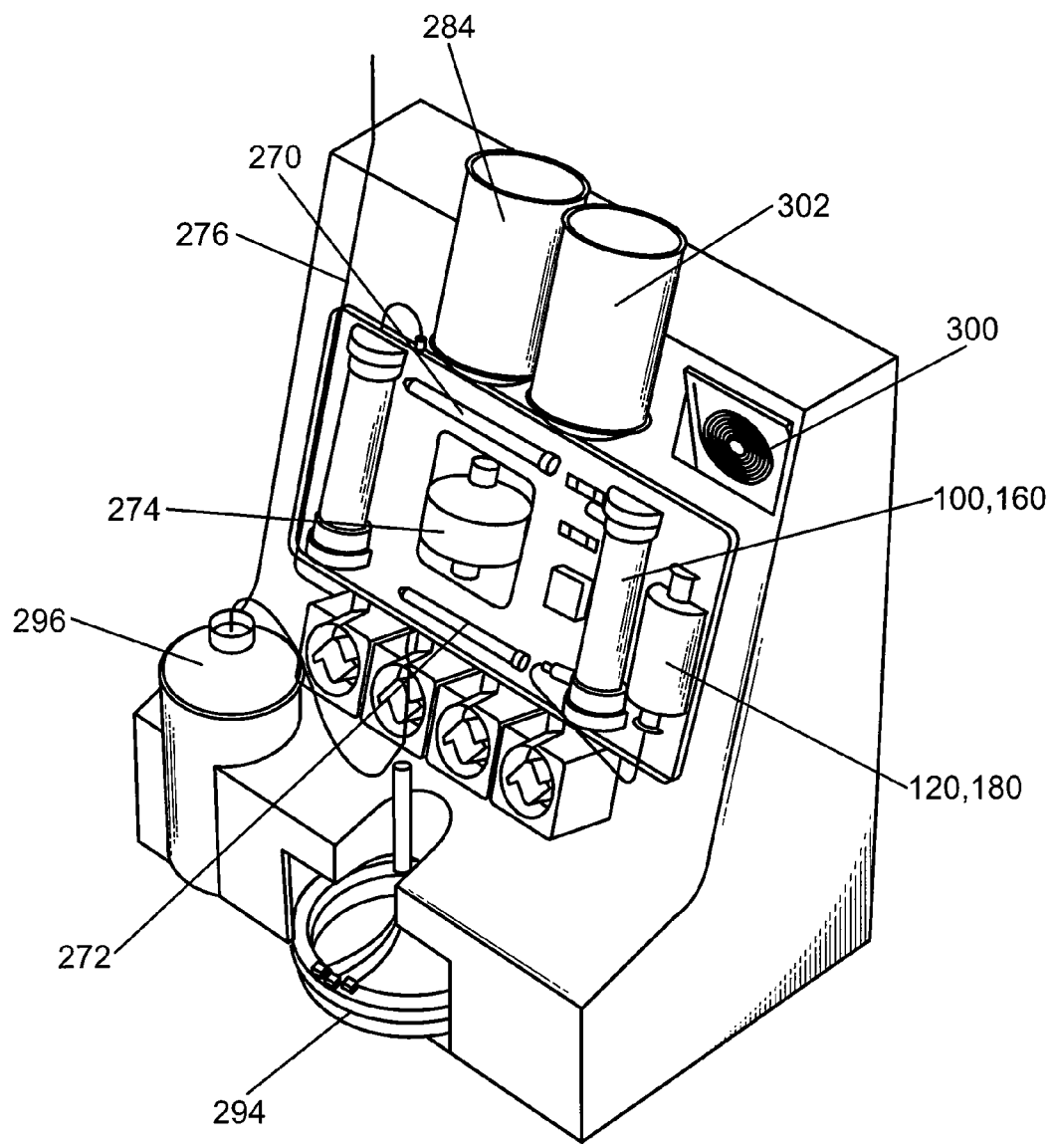
FIG. 19 is a perspective view of the device of FIG. 18 coupled to a delipidation system.

This embodiment described above may be assembled in a module that resembles module 306 depicted in FIGS. 18 and 19. The module contains the components of delipidation system 10 through which the fluid flows. In one embodiment, the module is disposable, which enables the system to be set up quickly after having been used. The device is prepared for use with another patient's fluid by simply removing the module and replacing it with an unused sterile module or a module that is sterilized following a prior use.

2. Method of Operation

This embodiment combines a fluid, which preferably is plasma, and at least one first extraction solvent. In this example, the first extraction solvent may be composed of about 40 percent n-butanol and about 60 percent di-isopropyl ether (DiPE). The fluid is mixed, agitated or otherwise contacted with the first extraction solvent to remove a portion of the lipids or lipid-containing organisms from the fluid. A small batch of the plasma, which is typically about 250 milliliters, is passed through the lumens of hollow fibers 312 of HFC 310 at a flow rate of about 20 mL/min. HFC 310 provides a method of contacting the plasma with the first extraction solvent while essentially keeping the two mixtures separated. However, a portion of the first extraction solvent crosses the pores of HFC 310 and does not return to the shell side of hollow fibers 312 and thus forms a first mixture. The first mixture is recirculated through HFC 310 at the same flow rate, which is usually about 20 mL/min.

The first extraction solvent is then substantially removed from the plasma before being administered to a patient. First, the flow of plasma is stopped, and the first extraction solvent is removed from the shell side of the HFC. A second extraction solvent is then sent through the shell side of the hollow fibers of the HFC. The second extraction solvent may be composed of about 100 percent isopropyl ether, about 100 percent ethyl ether, or any other ether or concentration of these ethers. Desirable properties of the ethers include, but are not limited to, reduced toxicity, higher vapor pressure, and a partition coefficient that is favorable with n-butanol. The second extraction solvent does not recirculate as does the first extraction solvent. Instead, the second extraction solvent flows through HFC 310 only one time at a rate of about 40 mL/min. The first mixture is sent through HFC 310 multiple times at a rate of about 20 mL/min for about 90 minutes. The second extraction solvent crosses the membrane of the hollow fibers of the HFC and mixes with the first mixture of plasma and first extraction solvent to form a second mixture. In one embodiment in which the first extraction solvent is a mixture of n-butanol and DiPE, the second extraction solvent removes at least a portion of the n-butanol from the first mixture. In addition, the second extraction solvent may remove a portion of the remaining lipids from the fluid. The second extraction solvent is then removed by, for instance evaporating the second wash solvent from the plasma using a pervaporation system, such as the subsystems shown in FIGS. 9 and 10.

E. Fifth Embodiment

Figure 20:
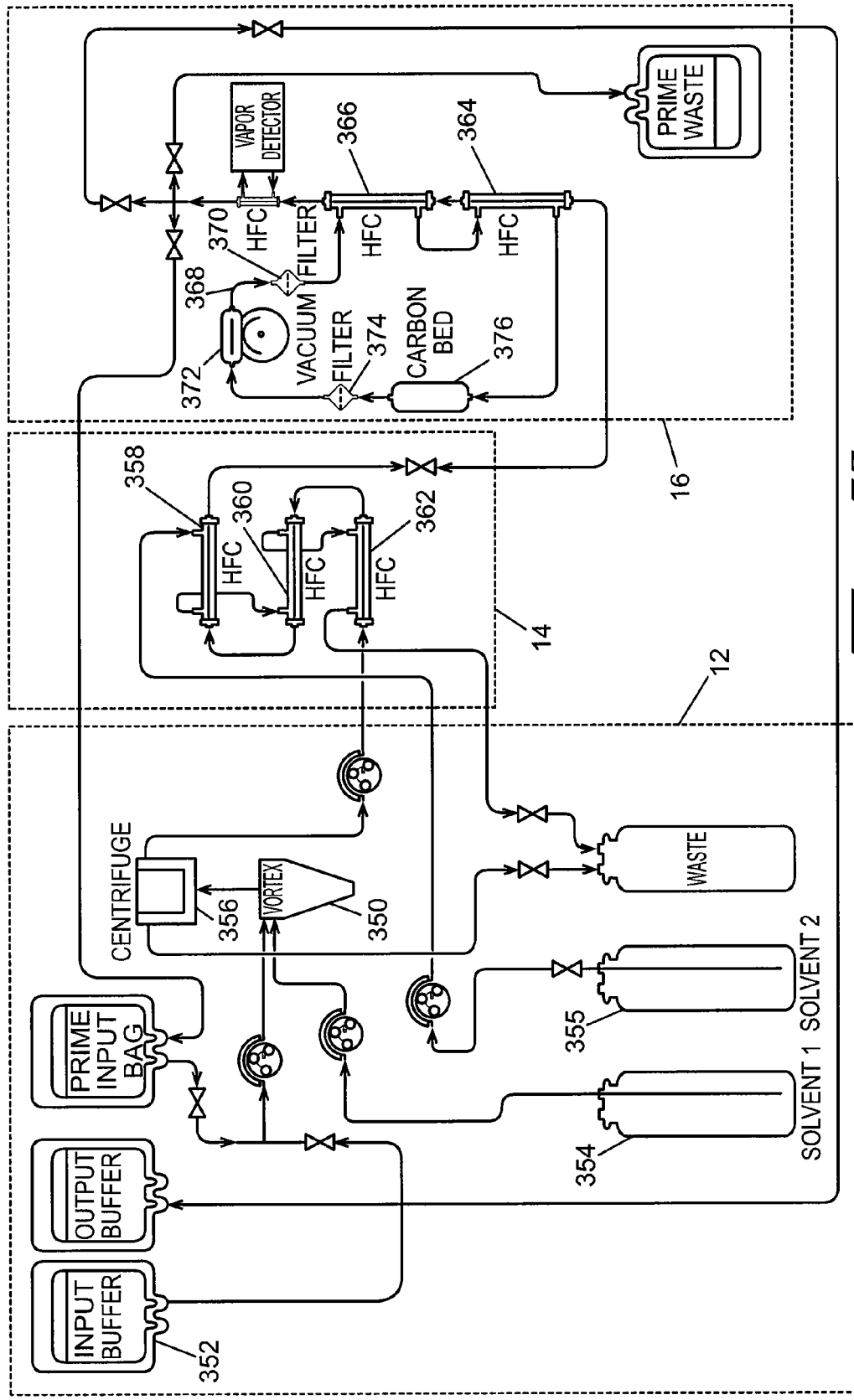
FIG. 20 is a schematic diagram of a fifth embodiment of this invention showing an apparatus for removing lipids from a fluid or from a lipid-containing organism.

FIG. 20 depicts another embodiment of delipidation system 10 that includes initial, intermediate and final phase subsystems. Initial phase subsystem 12 includes at least one vortexer 350 for mixing a fluid containing lipids or lipid-containing organisms with a first extraction solvent. Vortexer 350 may be a continuous vortexer as shown in FIG. 6 or a batch vortexer as shown in FIG. 7. These vortexers operate upon receiving external vibration that causes vortices to form in each tube. The non-rotating vortexer 350 is advantageous because of its simplistic design that is less expensive than more complicated designs. Thus, it may be used more efficiently than other devices in a disposable system. Further, vortexer 350 does not contain any bushings, bearings or moving parts that are subject to failure. However, vortexer 350 may be formed from an alternative design. Initial phase subsystem 12 may also include centrifuge 356, which may be configured as shown in 8 or may be configured in another manner.

Vortexer 350 receives a fluid containing lipids or lipid-containing organisms from a fluid supply source 352 and mixes the fluid with a first extraction solvent received from a first extraction solvent source 354. Vortexer 350 forms a first mixture of first extraction solvent and fluid. Vortexer 350 also causes lipids to separate from the fluid or lipid-containing organisms. The lipids are removed and discarded, and the first mixture is sent to intermediate phase subsystem 14.

Intermediate phase subsystem 14 is composed of at least one HFC for contacting the first mixture with a second extraction solvent to remove at least a portion of the first extraction solvent from the first mixture. FIG. 20 shows three HFCs 358, 360, and 362, which may be configured as shown in FIGS. 3 and 4 and described in detail above. The first mixture may be sent through lumens of HFCs 358, 360, and 362, and a second extraction solvent, supplied from second extraction solvent source 355, may be sent through HFCs 358, 360, and 362 on the shell side of the lumens, or vice versa. HFCs 358, 360, and 362 removes at least a portion of the first extraction solvent from the first mixture and forms a second mixture of the fluid containing lipids or lipid-containing organisms and the first and second extraction solvents. The amount of surface area of hollow fibers required and the amount of residence time required for the fluid to reside in HFCs 358, 360, and 362 is calculated as set forth above. In embodiments having two or more HFCs 354, HFCs may be configures in parallel, series, any combination thereof, or any other configuration.

Intermediate phase subsystem 14 passes a second mixture of fluid and first and second extraction solvent to final phase subsystem 16. Final phase subsystem 16 removes substantially all of the second extraction solvent and any remaining first extraction solvent not removed in intermediate phase subsystem 14. Final phase subsystem 16 may be composed of any system capable of removing extraction solvents from a fluid containing lipids or lipid-containing organisms. Exemplary systems are shown in FIGS. 10 and 11 and described in III.A.3 (a) and (b), respectively and labeled as final phase subsystem 16 in FIG. 20. The embodiment shown in FIG. 20 includes two HFCs 364 and 366 for removing at least a portion of the first and second extraction solvents from the second mixture. A material such as, but not limited to, air, an inert gas, nitrogen and the like, or mineral oil may be circulated through HFCs 364 and 366 on the shell side of the lumens and through solvent removal subsystem 368. Solvent removal subsystem may include a first sterile filter 370, a vacuum pump 372, a second sterile filter 374, and one or more carbon beds 376.

F. Exemplary Embodiments

Figure 14:
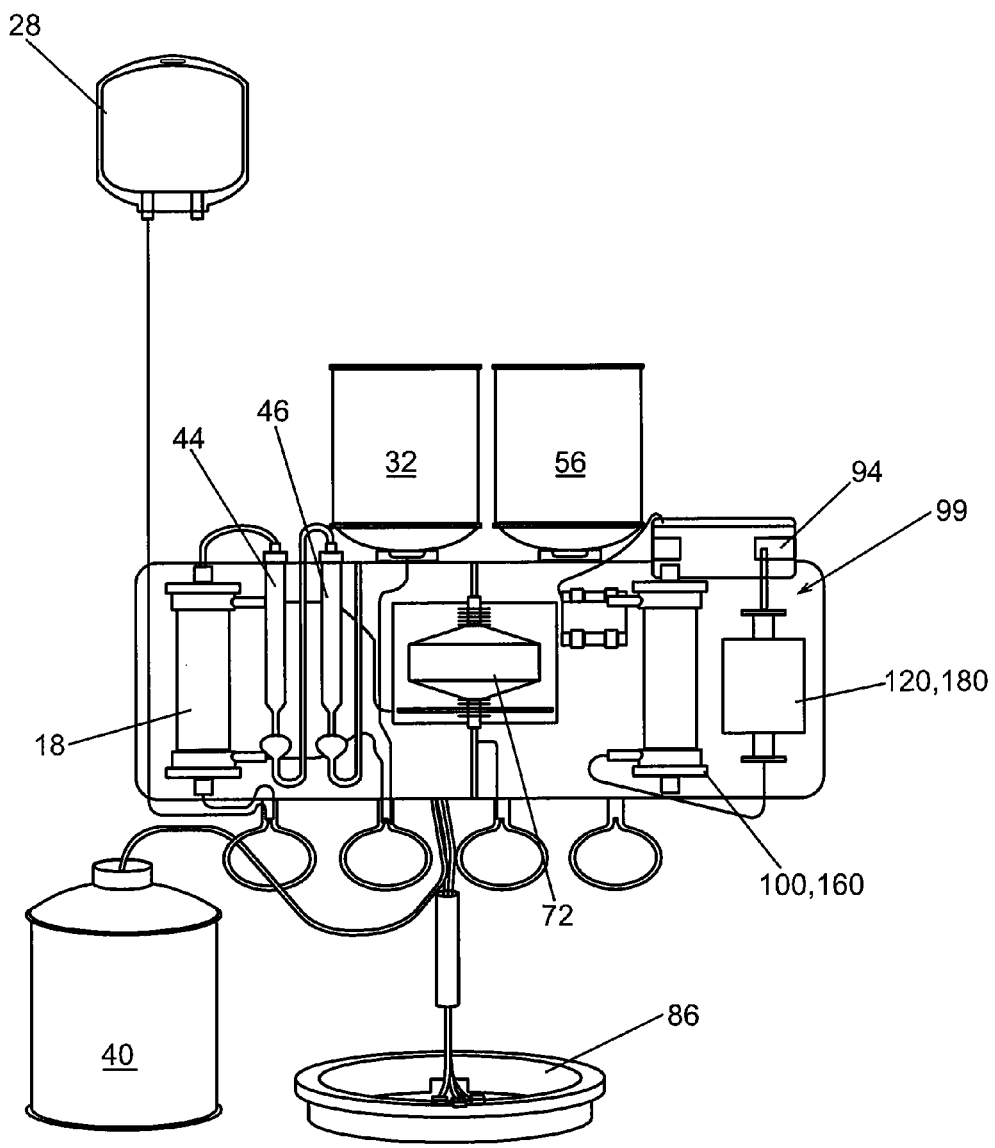
FIG. 14 is a schematicized perspective view of the device of FIG. 2 contained in a module.
Figure 15:
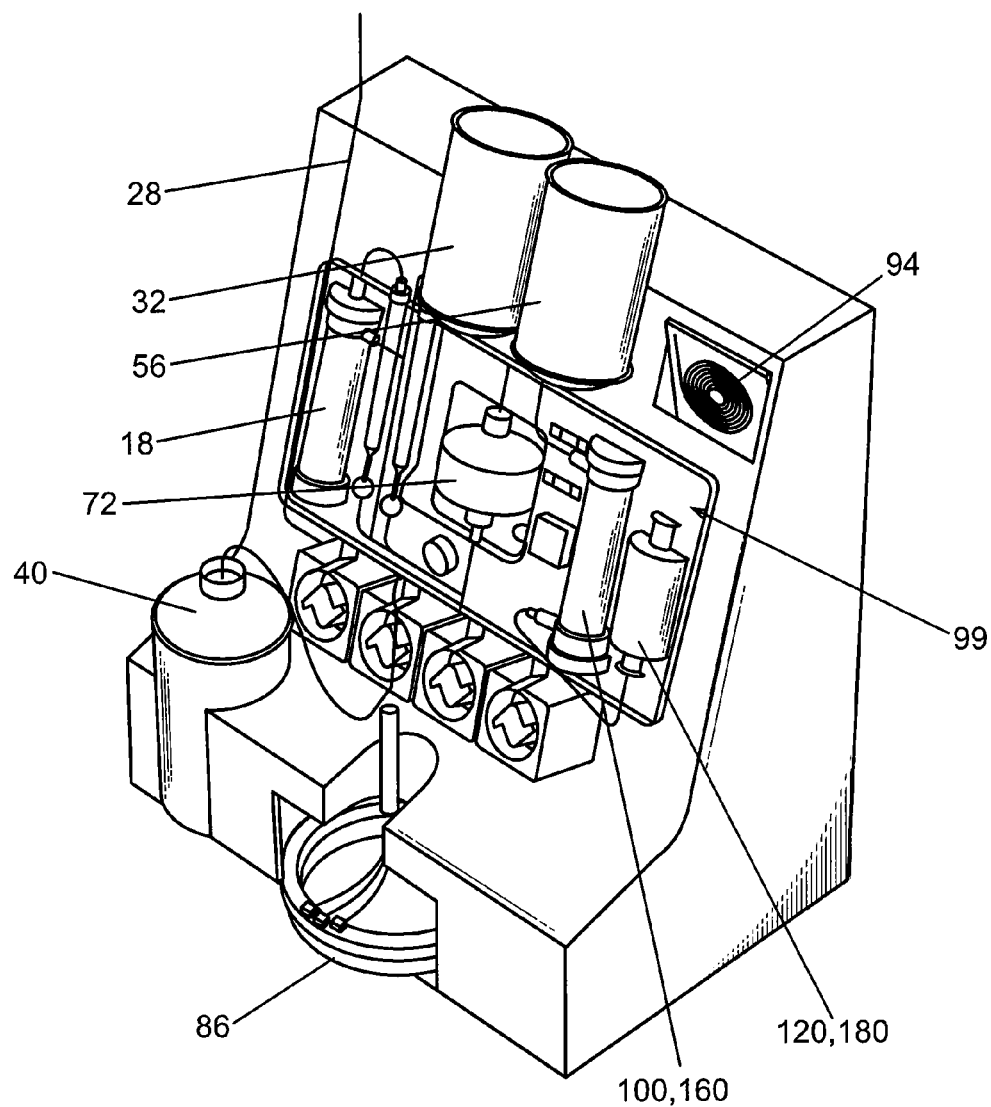
FIG. 15 is a perspective view of the device of FIG. 14 coupled to a delipidation system.
Figure 16:
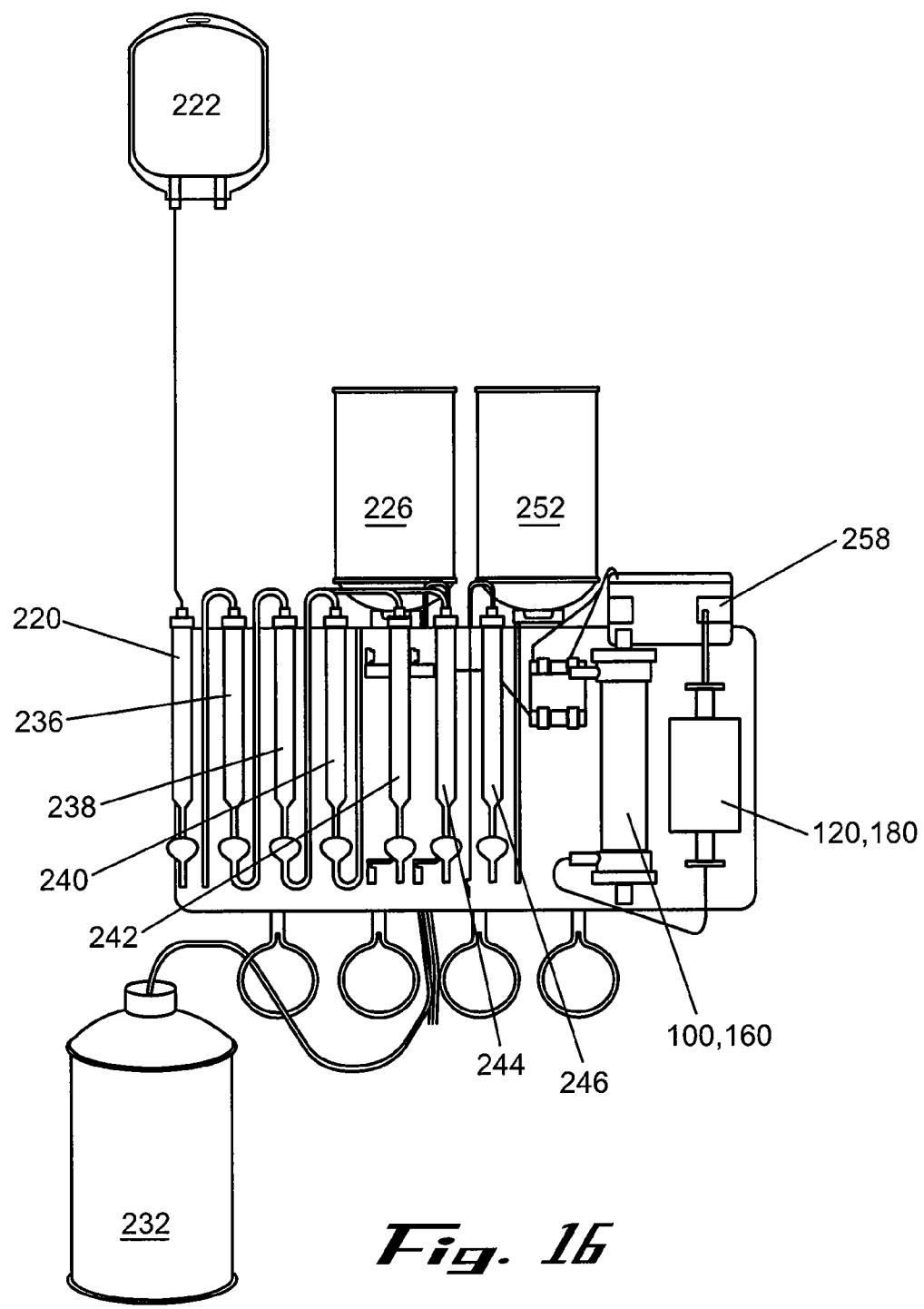
FIG. 16 is a schematicized perspective view of the device of FIG. 11 contained in a module.
Figure 17:
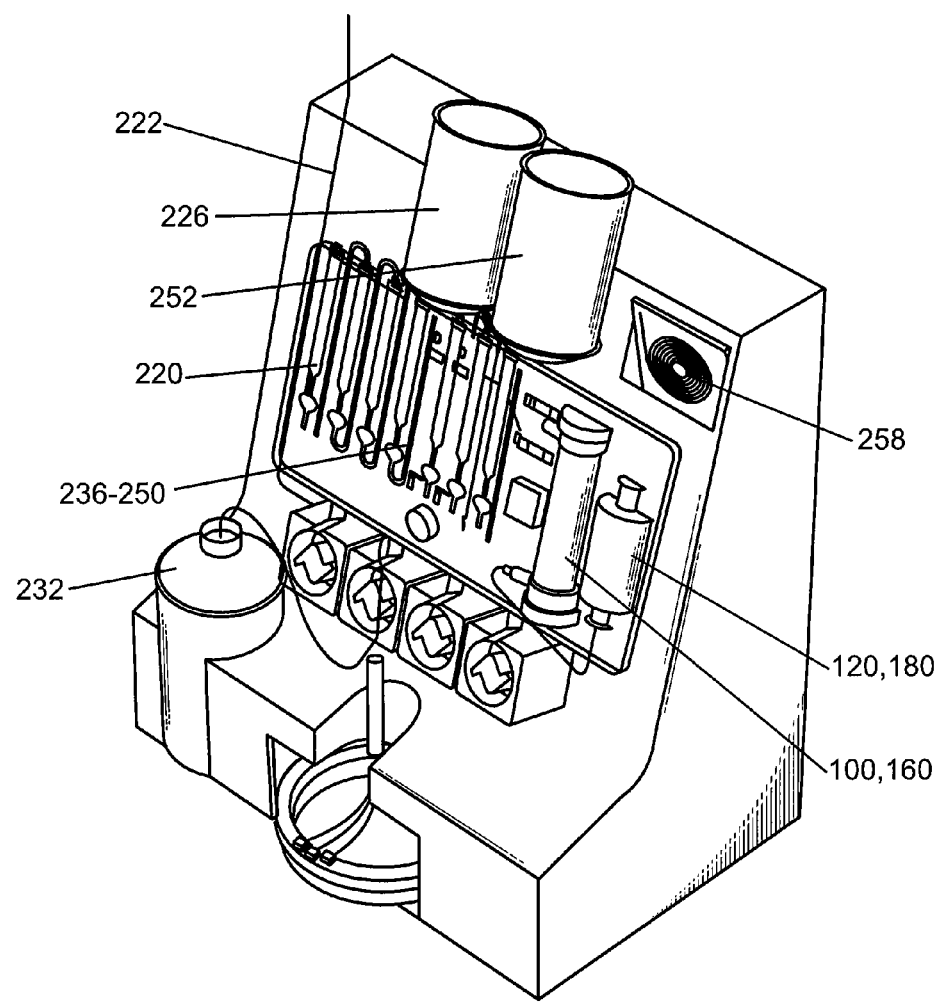
FIG. 17 is a perspective view of the device of FIG. 16 coupled to a delipidation system.

The embodiments described above may be manufactured so that all components that come in contact with a fluid containing lipids or lipid-containing organisms, or both, during operation are contained within a single module that may be disposable. The first embodiment described above may be assembled in a module 98, as depicted in FIGS. 14 and 15. The second embodiment described above may be assembled in a module 264, as depicted in FIGS. 16 and 17. The third embodiment described above may be assembled in a module 306, as depicted in FIGS. 18 and 19. Modules 98, 264 and 306 contain components of delipidation system 10 through which the fluid flows. To prevent the spread of diseases and for other health reasons, the delipidation system 10 should be cleaned after each use before being used with a fluid from a different source. In one embodiment, modules 98, 264 and 306 are disposable, which enables the system to be set up quickly after having been used. Delipidation device 10 may be prepared for use with another patient's fluid by simply removing a module and replacing it with a sterile module that may have never been used or may have been sterilized since a prior use.

G. Experimental Results

A system having an initial, intermediate, and final phase subsystems was employed. The initial phase subsystem was composed of three HFCs manufactured by Celguard. The intermediate phase subsystems was composed of three HFCs manufactured by Spectrum, and the final phase subsystem was composed of two HFCs manufactured by Celguard. All HFCs were oriented in series. Plasma was applied to the lumens of the HFCs. In the initial phase subsystem, the shell side of the HFCs contained a mixture of 40% butanol and 60% DIPE flowing in the same direction as the plasma flowing through the lumens of the HFCs at a rate of about 20 ml/min.

In the intermediate phase subsystem, 100 percent DiPE flowed through the HFCs on the shell side of the lumens at a rate of 40 ml per minute in a countercurrent direction to the direction of flow of the plasma through the lumens of the HFCs. In the final phase subsystem, air flowed through the three HFCs on the shell side of the lumens. Clinical chemistry data characterizing the parameters in the effluent delipidated plasma were obtained using a Hitachi 911. Results indicated dramatic reductions in cholesterol, triglycerides and HDL. Very little change or no change was observed in electrolytes (Na, Cl, and K), calcium, phosphorous, protein, albumin, globulin, phospholipids, creatinine, BUN, glucose, and alkaline phosphatase.

While various embodiments of this invention have been set forth above, these descriptions of the preferred embodiment are given for purposes of illustration and explanation.

Variations, changes, modifications, and departures from the systems and methods disclosed above may be adopted without departure from the spirit and scope of this invention.

We claim:

1. A device for removing at least one lipid from fluid containing lipids or lipid-containing organisms, comprising:
   at least one drip through column for contacting the fluid with a first extraction solvent, forming a first mixture comprising the fluid and the first extraction solvent, and dissolving at least a portion of the at least one lipid in the first extraction solvent;
   a first solvent removal device for contacting the first mixture with a second extraction solvent, removing at least a portion of the first extraction solvent, and forming a second mixture comprising the first extraction solvent, the second extraction solvent and the fluid; and
   a second solvent removal device for removing at least a portion of the second extraction solvent from the second mixture.

2. The device of claim 1, wherein the first solvent removal device comprises at least one hollow fiber contactor.

3. The device of claim 1, wherein the first solvent removal device comprises at least one drip through column.

4. The device of claim 1, wherein the first solvent removal device comprises at least one vortexer.

5. The device of claim 1, wherein the second solvent removal device comprises at least one hollow fiber contactor.

6. The device of claim 5, wherein the second solvent removal device comprises at least two hollow fiber contactors coupled together in parallel.

7. The device of claim 5, wherein the second solvent removal device comprises at least two hollow fiber contactors coupled together in series.

8. A device for removing at least one lipid from fluid containing lipids or lipid-containing organisms, comprising:
   a device for contacting the fluid with a first extraction solvent, forming a first mixture comprising the fluid and the first extraction solvent, and dissolving at least a portion of the at least one lipid in the first extraction solvent;
   at least one drip through column for contacting the first mixture with a second extraction solvent, removing at least a portion of the first extraction solvent, and forming a second mixture comprising the first extraction solvent, the second extraction solvent and the fluid; and
   a solvent removal device for removing at least a portion of the second extraction solvent from the second mixture.

9. The device of claim 8, wherein the device for contacting the fluid with a first extraction solvent comprises at least one hollow fiber contactor.

10. The device of claim 8, wherein the device for contacting the fluid with a first extraction solvent comprises at least one drip through column.

11. The device of claim 8, wherein the device for contacting the fluid with a first extraction solvent comprises at least one in-line static-mixer.

12. The device of claim 8, wherein the device for contacting the fluid with a first extraction solvent comprises at least one vortexer.

13. The device of claim 8, wherein the solvent removal device comprises at least one hollow fiber contactor.

14. The device of claim 13, wherein the solvent removal device comprises at least two hollow fiber contactors coupled together in parallel.

15. The device of claim 13, wherein the solvent removal device comprises at least two hollow fiber contactors coupled together in series.

16. A device for removing at least one lipid from fluid containing lipids or lipid-containing organisms, comprising:
   at least one drip through column for contacting the fluid with a first extraction solvent, forming a first mixture comprising the fluid and the first extraction solvent, and dissolving at least a portion of the at least one lipid in the first extraction solvent, and for contacting the first mixture with a second extraction solvent, removing at least a portion of the first extraction solvent, and forming a second mixture comprising the first extraction solvent, the second extraction solvent and the fluid; and
   a solvent removal device for removing at least a portion of the second extraction solvent from the second mixture, the solvent removal device comprising at least one hollow fiber contactor.

17. The device of claim 16, wherein the solvent removal device comprises at least two hollow fiber contactors coupled together in parallel.

18. The device of claim 16, wherein the solvent removal device comprises at least two hollow fiber contactors coupled together in series.

* * * * *